(12) United States Patent
Torgerson et al.

(10) Patent No.: US 10,300,282 B2
(45) Date of Patent: May 28, 2019

(54) ELECTRICAL STIMULATION THERAPY FOR INDUCING PATIENT SENSATIONS

(71) Applicant: Medtronic, Inc., Minneapolis, MN (US)

(72) Inventors: Nathan A. Torgerson, Andover, MN (US); Kevin L. Bright, Maple Grove, MN (US); Nicholas D. Buse, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/265,531

(22) Filed: Sep. 14, 2016

(65) Prior Publication Data

US 2017/0080233 A1    Mar. 23, 2017

Related U.S. Application Data

(60) Provisional application No. 62/220,790, filed on Sep. 18, 2015.

(51) Int. Cl.
*A61N 1/36* (2006.01)
*A61N 1/372* (2006.01)

(52) U.S. Cl.
CPC ....... *A61N 1/36132* (2013.01); *A61N 1/3615* (2013.01); *A61N 1/36067* (2013.01); *A61N 1/36071* (2013.01); *A61N 1/36125* (2013.01); *A61N 1/36167* (2013.01); *A61N 1/36192* (2013.01); *A61N 1/36196* (2013.01); *A61N 1/37235* (2013.01); *A61N 1/37247* (2013.01)

(58) Field of Classification Search
CPC .............. A61N 1/3605; A61N 1/36132; A61N 1/36135; A61N 1/37247
See application file for complete search history.

(56) References Cited

U.S. PATENT DOCUMENTS

| | | | |
|---|---|---|---|
| 5,487,759 A | 1/1996 | Bastyr et al. | |
| 7,689,289 B2 | 3/2010 | King | |
| 2002/0022866 A1* | 2/2002 | Borkan | A61N 1/056 607/59 |
| 2004/0037776 A1 | 2/2004 | Lacharriere et al. | |
| 2004/0249422 A1 | 12/2004 | Gliner et al. | |
| 2008/0051839 A1 | 2/2008 | Libbus et al. | |

(Continued)

FOREIGN PATENT DOCUMENTS

| | | |
|---|---|---|
| WO | 2004052451 A1 | 6/2004 |
| WO | 2007081284 A1 | 7/2007 |

(Continued)

OTHER PUBLICATIONS

Tan, et al., "A neural interface provides long-term stable natural touch perception," Sci Transl Med 6, access from stm.sciencemag.org, on Oct. 8, 2014, 12 pp.

(Continued)

*Primary Examiner* — Rex R Holmes
(74) *Attorney, Agent, or Firm* — Shumaker & Sieffert, P.A.

(57) ABSTRACT

Electrical stimulation therapy is provided to a patient in order to induce a patient sensation. The patient sensation may be selected from a number of patient sensations. A set of therapy parameter values are associated with each of the number of patient sensations. A user interface allows a user to adjust one or more characteristics of the patient sensation.

14 Claims, 14 Drawing Sheets

(56) References Cited

U.S. PATENT DOCUMENTS

| | | |
|---|---|---|
| 2008/0103559 A1 | 5/2008 | Thacker et al. |
| 2009/0270947 A1 | 10/2009 | Stone et al. |
| 2010/0274320 A1 | 10/2010 | Torgerson |
| 2011/0071589 A1 | 3/2011 | Starkebaum et al. |
| 2011/0175717 A1 | 7/2011 | Drong et al. |
| 2011/0313487 A1 | 12/2011 | Kokones et al. |
| 2012/0022612 A1 | 1/2012 | Littlewood et al. |
| 2013/0138176 A1 | 5/2013 | Goetz et al. |
| 2014/0067017 A1 | 3/2014 | Kaula et al. |
| 2014/0276549 A1 | 9/2014 | Osorio |
| 2015/0039048 A1 | 2/2015 | Woods et al. |
| 2016/0051817 A1 | 2/2016 | Popovic et al. |
| 2016/0361551 A1 * | 12/2016 | Kaula ............... A61N 1/3605 |

FOREIGN PATENT DOCUMENTS

| | | | | |
|---|---|---|---|---|
| WO | WO2007/081284 A1 * | 7/2007 | ............... | A61N 1/00 |
| WO | 2008121891 A1 | 10/2008 | | |

OTHER PUBLICATIONS

International Search Report and Written Opinion from International Application No. PCT/US2016/051950, dated Dec. 23, 2016, 13 pp.

International Search Report and Written Opinion from International Application No. PCT/US20016/051957, dated Jan. 2, 2017, 10 pp.

International Preliminary Report on Patentablity from International Application No. PCT/US2016/051957, dated Mar. 29, 2018, 8 pp.

Office Action from U.S. Appl. No. 15/265,480, dated Nov. 24, 2017, 15 pp.

Response to Office Action dated Nov. 24, 2017, from U.S. Appl. No. 15/265,480, filed Feb. 21, 2018, 12 pp.

Office Action from U.S. Appl. No. 15/265,480, dated Mar. 19, 2018, 33 pp.

Examination Report from counterpart Australian Patent Application No. 2016323311, dated Jun. 20, 2018, 3 pp.

Response to Office Action dated Mar. 19, 2018, from U.S. Appl. No. 15/265,480, filed Jun. 4, 2018, 20 pp.

Final Office Action from U.S. Appl. No. 15/265,480, dated Jul. 30, 2018, 14 pp.

Office Action from U.S. Appl. No. 15/265,480, dated Nov. 19, 2018, 14 pp.

Response to counterpart Australian Patent Application 2016323311, filed on Sep. 6, 2018, 15 pp.

Response to Final Office Action dated Jul. 30, 2018, from U.S. Appl. No. 15/265,480, filed Sep. 28, 2018, 14 pp.

Advisory Action from U.S. Appl. No. 15/265,480, dated Oct. 5, 2018, 4 pp.

* cited by examiner

ELECTRICAL STIMULATION THERAPY FOR INDUCING PATIENT SENSATIONS

CROSS-REFERENCE TO RELATED APPLICATION

This application claims the benefit of U.S. Prov. Pat. App. Ser. No. 62/220,790, filed 18 Sep. 2015 and entitled ELECTRICAL STIMULATION THERAPY FOR INDUCING PATIENT SENSATIONS, the entirety of which is hereby incorporated by reference.

TECHNICAL FIELD

The disclosure relates to electrical stimulation therapy.

BACKGROUND

Some medical devices are used to deliver electrical stimulation therapy to patients to treat a variety of symptoms or conditions, such as chronic pain, tremor, Parkinson's disease, epilepsy, gastroparesis, urinary or fecal incontinence, and sexual dysfunction. The electrical stimulation is generally delivered to selected target tissues or locations in a patient's body, such as the brain, the spinal cord, pelvic nerves, or peripheral nerves. Hence, stimulation is used in different therapeutic applications, such as spinal cord stimulation (SCS), deep brain stimulation (DBS), gastric stimulation, pelvic stimulation, or peripheral nerve stimulation. Medical devices have also been used to deliver electrical stimulation to the heart, e.g., for cardiac pacing, and muscles, e.g., for functional electrical stimulation (FES) to promote muscle movement or prevent muscle atrophy.

SUMMARY

In general, the disclosure is directed to techniques for adjusting parameters associated with electrical stimulation therapy to induce a patient sensation, such as a tactile sensation. Although not so limited, a number of example implementations of such techniques are contemplated, such as:

A patient programmer comprising a user interface configured to display a plurality of different stimulation sensations, and receive user input that represents a selection of a stimulation sensation from among the plurality of different stimulation sensations, and a processor configured to in response to the user input, select a value of at least one therapy parameter from a set of therapy parameters to control a medical device to deliver stimulation configured to induce the selected stimulation sensation, wherein the plurality of different stimulation sensations are associated with respective values of the therapy parameters.

Optionally, the user interface is configured to receive user input that represents an adjustment of the selected value of the at least one therapy parameter, and wherein the processor is configured to adjust the selected value of the at least one therapy parameter to control the medical device to deliver stimulation in accordance with the adjustment of the selected value.

Optionally, the patient programmer further comprises telemetry circuitry configured to transmit the selected value to the medical device which is configured to deliver stimulation in accordance with the selected value to induce the selected stimulation sensation.

Optionally, the selected value of the at least one therapy parameter is a time modulated value.

Optionally, the set of therapy parameters comprises at least one of stimulation pulse width or stimulation pulse amplitude.

Optionally, the user interface is configured to display an interactive control to receive the user input, and wherein the user input further represents an adjustment of the interactive control that is representative of an adjustment of intensity of the selected stimulation sensation, and the processor is configured to adjust the selected value of the at least one therapy parameter to control the medical device to deliver stimulation in accordance with the adjustment of intensity of the selected stimulation sensation.

Optionally, the stimulation sensation is selected from at least one of a constant pressure sensation, a pulsing pressure sensation, a vibration sensation, a tapping sensation or a moving touch sensation.

Optionally, the set of therapy parameters comprises a modulation of at least one of stimulation pulse width or stimulation pulse amplitude, and the processor is configured to select one of stimulation pulse width and stimulation pulse amplitude for adjustment in response to user input that represents a selection of one of stimulation pulse width and stimulation pulse amplitude for adjustment.

Optionally, adjustment of stimulation pulse width or stimulation pulse amplitude comprises adjustment of one of modulation frequency, modulation variance, interpulse interval or interpulse intensity.

A method comprising, by a patient programmer, outputting for display a plurality of different stimulation sensations, receiving user input that represents a selection of a stimulation sensation from among the plurality of different stimulation sensations, selecting a value of at least one therapy parameter from a set of therapy parameters to control a medical device to deliver stimulation configured to induce the selected stimulation sensation, wherein the plurality of different stimulation sensations are associated with respective values of the therapy parameters, and in response to a command, transmitting the value of the at least one therapy parameter value to the medical device to control the medical device to induce the selected stimulation sensation.

Optionally, the method further comprises receiving user input that represents adjustment of the selected value of the at least one therapy parameter, adjusting the selected value of the at least one therapy parameter, and transmitting the selected value as adjusted to the medical device to control the medical device to deliver stimulation in accordance with the adjustment of the selected value.

Optionally, the method further comprises transmitting the selected value as adjusted to the medical device to control the medical device to deliver stimulation in accordance with the adjustment of the selected value.

Optionally, the selected value of the at least one therapy parameter is a time modulated value.

Optionally, the set of therapy parameters comprises at least one of stimulation pulse width or stimulation pulse amplitude.

Optionally, the method further comprises outputting for display an interactive control to receive the user input, and wherein the user input further represents an adjustment of the interactive control that is representative of an adjustment of intensity of the selected stimulation sensation, and adjusting the selected value of the at least one therapy parameter to control the medical device to deliver stimulation in accordance with the adjustment of intensity of the selected stimulation sensation.

Optionally, the stimulation sensation is selected from at least one of a constant pressure sensation, a pulsing pressure sensation, a vibration sensation, a tapping sensation or a moving touch sensation.

Optionally, the set of therapy parameters comprises a modulation of at least one of stimulation pulse width or stimulation pulse amplitude, and the method further comprises selecting one of stimulation pulse width and stimulation pulse amplitude for adjustment in response to user input that represents a selection of one of stimulation pulse width and stimulation pulse amplitude for adjustment.

Optionally, the method further comprises receiving the user input that represents the selection of one of stimulation pulse width and stimulation pulse amplitude for adjustment, in response to receiving the user input, outputting for display an interactive control to adjust one of modulation frequency, modulation variance, interpulse interval or interpulse intensity, receiving user input that represents adjustment of the interactive control, and adjusting the one of the modulation frequency, modulation variance, interpulse interval or interpulse intensity to control the medical device to deliver stimulation in accordance thereof.

A system comprising a patient programmer and a medical device, wherein the patient programmer is configured to output for display a plurality of different stimulation sensations, receive user input that represents a selection of a stimulation sensation from among the plurality of different stimulation sensations, select a value of at least one therapy parameter from a set of therapy parameters to control a medical device to deliver stimulation configured to induce the selected stimulation sensation, wherein the plurality of different stimulation sensations are associated with respective values of the therapy parameters, and transmit the value of the at least one therapy parameter value to the medical device to control the medical device to induce the selected stimulation sensation.

Optionally, the medical device is configured to receive from the patient programmer the value of the at least one therapy parameter, and generate stimulation in accordance with the value of the at least one therapy parameter to induce the selected stimulation sensation.

A non-transitory computer-readable storage medium comprising instructions, that when executed by processing circuitry of a patient programmer, cause the patient programmer to output for display a plurality of different stimulation sensations, detect user input that represents a selection of a stimulation sensation from among the plurality of different stimulation sensations, and based on the user input, select a value of at least one therapy parameter from a set of therapy parameters to control a medical device to deliver stimulation configured to induce the selected stimulation sensation, wherein the plurality of different stimulation sensations are associated with respective values of the therapy parameters.

A medical device or system comprising means for performing any of the methods or techniques described herein.

Non-transitory computer-readable media comprise program instructions that, when executed by processing circuitry of a medical device or system, cause the medical device or system to perform any of the methods or techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
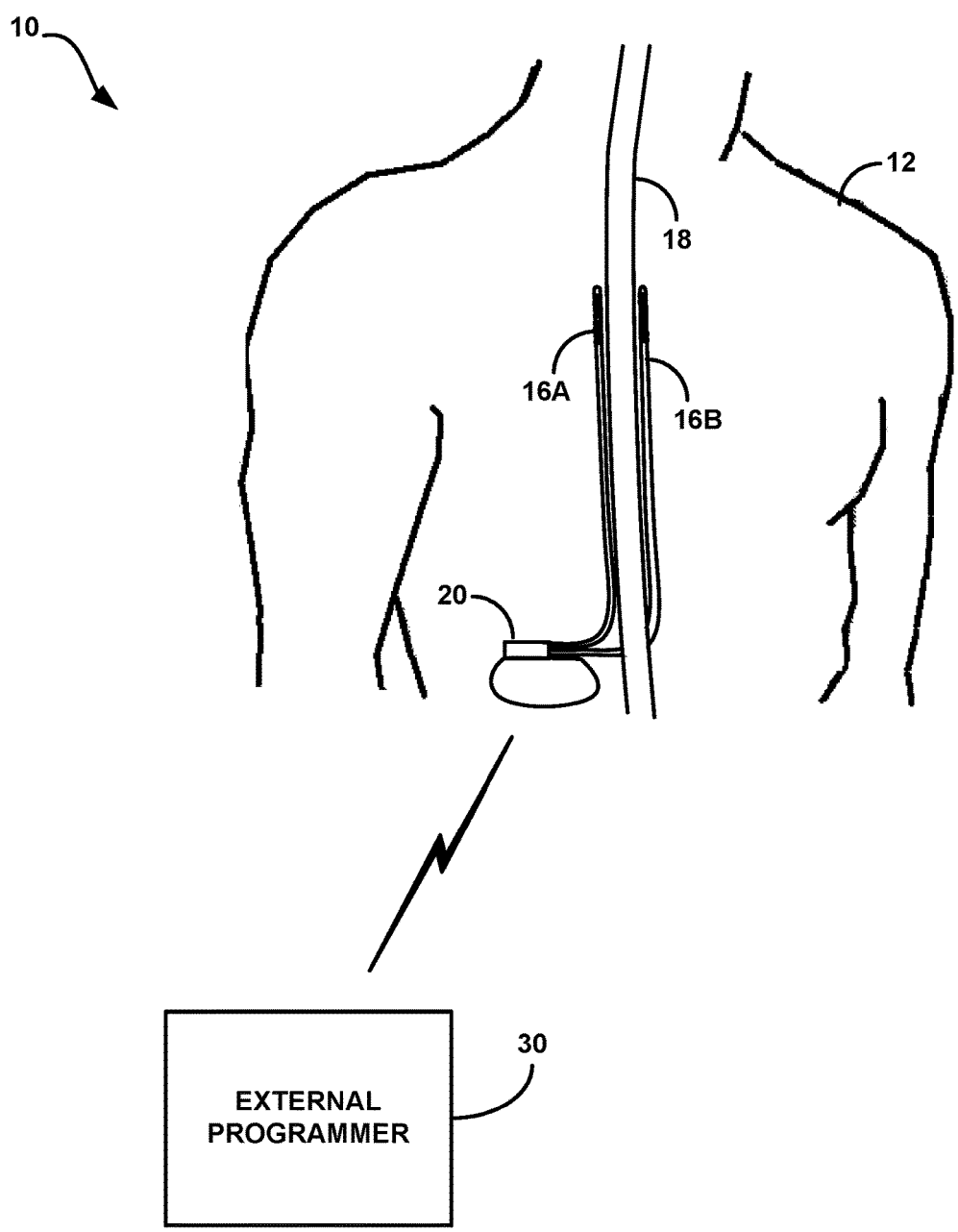
FIG. 1 is a conceptual diagram illustrating an example electrical stimulation therapy system.

Some medical devices are used to deliver electrical stimulation therapy to patients to treat a variety of symptoms or conditions, such as chronic pain, tremor, Parkinson's disease, epilepsy, gastroparesis, urinary or fecal incontinence, and sexual dysfunction. The electrical stimulation is generally delivered to selected target tissues or locations in a patient's body, such as the brain, the spinal cord, pelvic nerves, or peripheral nerves. Hence, stimulation is used in different therapeutic applications, such as spinal cord stimulation (SCS), deep brain stimulation (DBS), gastric stimulation, pelvic stimulation, or peripheral nerve stimulation. Medical devices have also been used to deliver electrical stimulation to the heart, e.g., for cardiac pacing, and muscles, e.g., for functional electrical stimulation (FES) to promote muscle movement or prevent muscle atrophy.

Such medical devices typically deliver electrical stimulation therapy in the form of electrical pulses. In many examples, the medical devices that deliver stimulation have been implantable. Implantable medical devices typically deliver electrical stimulation via one or more leads that include electrodes located proximate to target tissues. Implantable medical devices are often able to be communicated with and programmed using an external computing device, referred to a programming device or programmer, that wirelessly and transcutaneously communicates with the implantable medical device.

In most cases, a clinician creates one or more programs that a medical device will use to deliver therapy to a patient during an initial programming session. In the case of implantable medical devices, the initial programming session typically occurs shortly after the device is implanted in the patient. The values for each of the parameters of a program may have a significant impact on the efficacy and side effects of the delivery of electrical stimulation therapy according to that program. The process of selecting values for the parameters that provide adequate results can be time consuming. In particular, the process may require a great deal of trial-and-error testing of numerous potential combinations of parameter values before a "best" program is discovered. For example, a "best" program may be a program that is better in terms of clinical efficacy versus side effects experienced than other programs tested. As another example, a best program may also be a program that requires relatively less energy than other programs, such that energy consumed by the electrical stimulation is minimized and power source longevity of the medical device is maximized.

In some cases, the clinician may need to test a large number of possible electrode configurations, i.e., combinations and polarities, in order to identify a desirable configuration. During the testing of an electrode configuration, the clinician may select a pulse width, and then adjust amplitude to identify one or more amplitude thresholds, such as the amplitude at which stimulation is first perceived by the patient (or perception threshold), and the maximum amplitude at which stimulation is still comfortable or the amplitude at which side effects from stimulation become intolerable. A usage range, e.g., a range of amplitudes useable for stimulation therapy, may be defined based on these amplitude thresholds. Additionally or alternatively, the clinician may identify a usage amplitude, which may be an amplitude at which stimulation is effective and results in minimal, tolerable, or no side effects. The clinician may select the pulse-width based on intuition or experience. The clinician may repeat the time-consuming amplitude adjustment process for the electrode configuration with one or more other fixed pulse widths, or may proceed to another electrode configuration after having tested only one pulse width.

Even after this often-lengthy process, the programs selected during an initial programming session may ultimately prove to be inadequate. The eventual inadequacy of the initial programming may be due to a variety of problems, including progression of symptoms and/or an underlying ailment, increased or changed symptoms or side effects during activities and/or postures that were not replicated in the clinic during the initial programming session, slow onset of side effects and, in the case of delivery of stimulation via electrodes located on implantable leads, lead migration.

Patients have been given the ability to adjust stimulation outside of the clinic, at least in part to address such situations. For example, patients with implantable medical devices have been provided an external programming device, referred to as a patient programmer or patient therapy manager, that is simplified relative to the programming device used by a clinician. The patient may use the patient programmer to adjust some parameters of the stimulation, such as amplitude or selected program, although often in a manner that is restricted relative to the clinician.

The disclosure is directed to techniques for providing electrical stimulation therapy to a patient which provides a particular desired sensation to a patient. In some examples, a user, such as a clinician, may select different desired sensations to be produced by electrical stimulation delivered to the patient. In some examples, a user adjusts characteristics of a selected sensation to be produced by electrical stimulation delivered to the patient. In some examples, the selected sensation may be a non-paresthesia sensation, i.e., a sensation other than paresthesia, numbness, and/or tingling.

For example, one or more parameters of the electrical stimulation may be adjusted to produce a sensation of constant pressure, pulsing pressure, vibration, tapping, moving touch, or other types of sensations. Each sensation may be created by variations in one or more stimulation parameters. For example, at least one of pulse width, amplitude, or frequency of stimulation may be varied according to a set of stimulation therapy parameters in order to achieve the desired type of sensation. In some examples, the set of stimulation therapy parameters may be a therapy program. In addition, for a given type of sensation, one or more of the therapy parameters may be adjusted to produce different characteristics of the sensation, such as different intensities, frequencies, modulation frequency, modulation variance, or the like.

In some examples, the system includes a user interface which allows a user, such as a patient or clinician, to adjust a characteristic of the desired sensation. For example, the user interface may allow the user to increase the strength of pressure being felt, or the frequency of the sensation, such as the frequency of tap or touch sensations. In some examples, the user may enter an adjustment to the characteristic without directly adjusting a stimulation parameter that influences the characteristic. Instead, based on the adjustment to the characteristic of the sensation, a processor automatically adjusts one or more of the therapy parameters of the therapy program to achieve the desired sensation. For example, the processor may adjust the strength of pressure felt by the patient by adjusting the amplitude parameter of stimulation pulses applied to the patient, while maintaining the values of the other stimulation parameters at existing values. As another example, the processor may adjust the perceived frequency of the sensation by adjusting parameters such as the pulse width of stimulation pulses, the duration of bursts of multiple stimulation pulses, the time between successive pulses, i.e., inter-pulse interval, the time between successive pulse bursts, i.e., inter-burst interval, or any combination of such parameters. In other examples, the desired change in sensation may require multiple interrelated adjustments to two or more of the stimulation parameters. For example, the processor also may adjust intensity by adjusting one or more of pulse amplitude, pulse width, burst duration, inter-pulse interval, or inter-burst interval, alone or in any combination.

In general, adjustment may refer to an increase or decrease in a perceived characteristic(s) of the sensation. Likewise, adjustment may refer to an increase or a decrease in a given parameter as appropriate to achieve the desired increase or decrease in a perceived characteristic(s) of the sensation produced by the stimulation. In some cases, an increase in a parameter may increase a characteristic(s), or a decrease in the parameter may increase the characteristic(s). Likewise, in some cases, a decrease in a parameter may decrease a characteristic(s), or an increase in the parameter may decrease the characteristic(s).

A user interface may present a user-friendly mechanism for changing one or more characteristics of a stimulation sensation. For example, the user interface may allow a user to adjust an icon along a sliding scale of possible values of a characteristic. In other examples, a user may enter a value within a predefined range, press an up or down arrow, or press a plus or minus sign in order to change characteristics. Again, examples of sensation characteristics include, without limitation, perceived sensation intensity and sensation frequency. Sensation intensity may be perceived as a sensation of pressure. The therapy programs associated with each sensation may include a plurality of stimulation parameters such as pulse width, amplitude, and frequency, at least one of which varies over time as part of a therapy program. Other stimulation parameters may include inter-pulse interval, burst duration or inter-burst interval. Additional stimulation parameters may include electrode configuration, including the combination of electrodes selected from an array of electrodes to deliver stimulation, and the polarities of such electrodes. In some examples, the number of electrodes selected, and the positions of the electrodes, may influence one or more characteristics of the sensation, either alone or in combination with other parameters. Accordingly, an apparently minor parameter adjustment, such as an increase in stimulation intensity, may actually be computationally intensive as the stimulation parameter values of each of a plurality of different stimulation pulses must be changed. For example, the charge intensity for a particular pulse may be equal to the pulse width multiplied by pulse amplitude. As the pulse width and amplitude are multiplied to achieve the intensity, an increase to the intensity may not result in the same value increase to pulse amplitude for each of a plurality of pulse widths.

A system according to this disclosure may store, and deliver stimulation according to, a set of therapy parameter sets or therapy programs associated with different stimulation sensations which include initial stimulation parameter values. In addition, the system may store ranges of stimulation parameter values resulting in efficacious stimulation therapy. The ranges of stimulation parameter values may be determined during initial programming of an implantable medical device. The range of stimulation parameter values may include a stimulation intensity perception threshold and a stimulation intensity pain threshold. The stimulation intensity perception threshold may correspond to the value of stimulation intensity which first captures the nerve and result in perception of the stimulation by the patient. The stimulation intensity pain threshold may correspond to the stimulation intensity value at which the patient first perceives pain in response to the application of stimulation. The initial programming may include a determination of a minimum stimulation intensity which results in the desired stimulation sensation. This minimum stimulation intensity may be different than the stimulation intensity perception threshold. For example, for pulsing pressure sensation, the intensity may need to be higher than the perception threshold for a single pulse in order to allow for a variation in intensity that results in the pulsing sensation. In addition, the range of intensities may be different than for a therapy program with consistent parameter values because at the extremes of amplitude and pulse width, nerve capture may change. During initial programming a range of intensities may be determined which allow the corresponding stimulation parameter values of the therapy program to not only capture a target nerve, but allow the relationship between pulse amplitude and pulse width to be maintained with an ideal range for each of the different pulse widths associated with the therapy program. For example, intensities may be limited in order to maintain the stimulation within a range around the "knee" of a typical strength-duration curve for target neural tissue.

In some examples, the electrical stimulation therapy is provided to a patient in order to control pain. The stimulation may be spinal cord stimulation (SCS), peripheral nerve stimulation (PNS), pelvic floor stimulation, or deep brain stimulation (DBS), for example.

Figure 2:
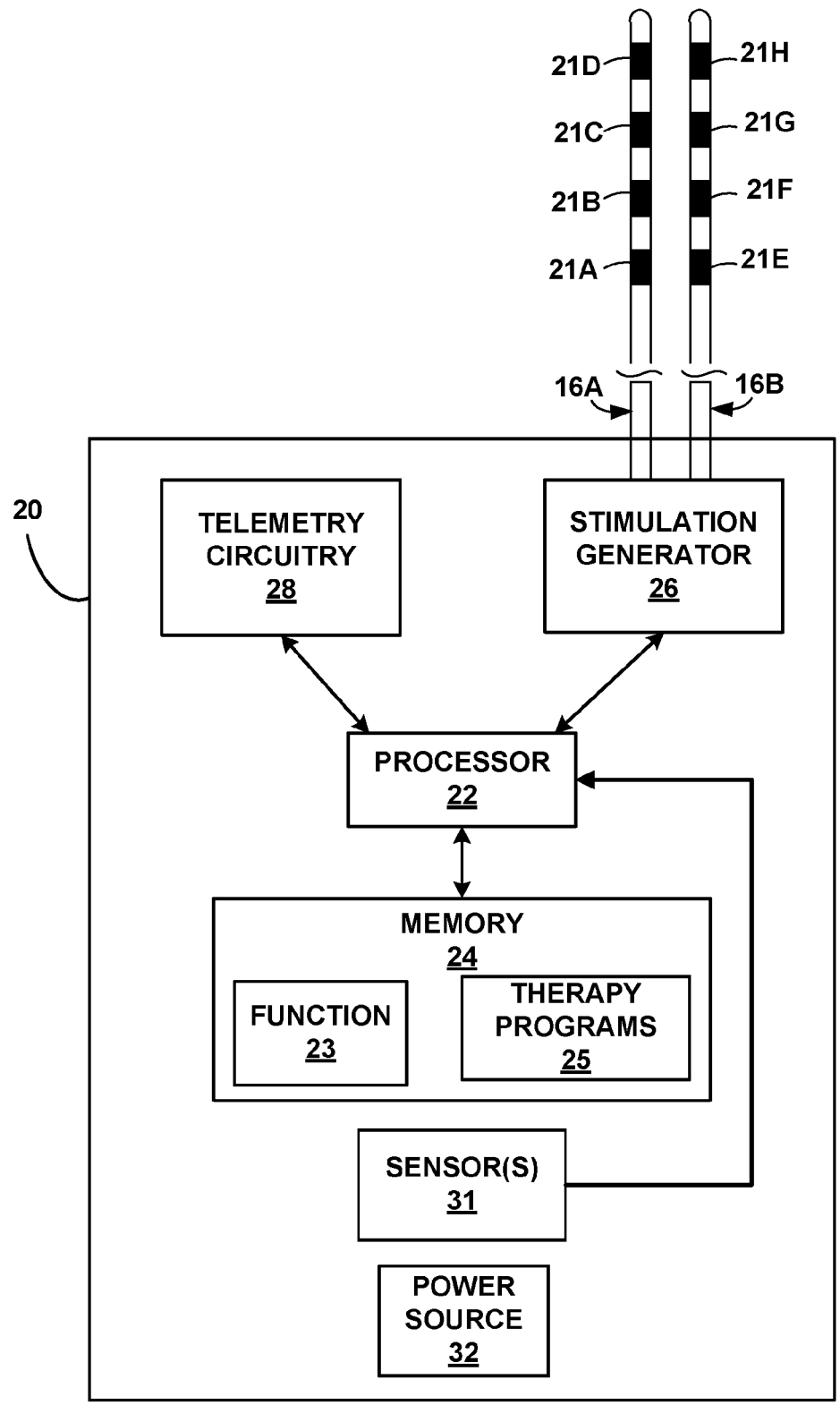
FIG. 2 is a block diagram illustrating an example configuration of an implantable medical device that delivers electrical stimulation therapy.

FIG. 1 is a conceptual diagram illustrating an example stimulation therapy system 10 that delivers therapeutic electrical stimulation to patient 12. Therapy system 10 includes an implantable medical device (IMD) 20, which is coupled to leads 16A and 16B (collectively "leads 16"), and communicates with an external programmer 30. Leads 16 each include one or more electrodes (FIG. 2). IMD 20 delivers electrical stimulation to patient 12 via the electrodes. The illustrated number and location of leads is merely one example. Furthermore, the techniques described herein may be implemented using systems in which the medical device and/or leads are not implantable, or which do not include leads and/or a programmer.

In the illustrated example, IMD 20 delivers spinal cord stimulation (SCS) to the spinal cord 18 of patient 12 to, for example, treat chronic pain. In other examples, IMD 20 or another medical device delivers cortical stimulation (CS), peripheral nerve stimulation (PNS), sacral nerve stimulation, or peripheral nerve field stimulation (PNFS). Stimulation may be configured to provide sensations to support therapy for a variety of symptoms, diseases and disorders, such as chronic pain, temporary pain, movement disorders, epilepsy, depression, anxiety, or the like. Thus, the techniques for stimulation programming are described with respect to system 10 and SCS, but without limitation as to application of such techniques to other systems, target stimulation sites, or therapy applications.

A user, such as a clinician or patient, interacts with programmer 30 to configure the electrical stimulation delivered by IMD 20. In this manner, programmer 30 controls the stimulation delivered by IMD 20. In various examples, programmer 30 comprises a handheld device, portable computer, or workstation that provides a user interface to a clinician. Programmer 30 communicates with IMD 20 using any medical device telemetry or other wireless communication techniques known in the art. In some examples, programmer 30 is a remote device that communicates with IMD 20 via a network. Programmer 30 may be a relatively full-featured clinician programmer, or a patient programmer with relatively limited control over the operation of IMD 20.

The patient or clinician interacts with programmer 30 to program stimulation parameters. In some examples, the clinician determines acceptable and efficacious stimulation intensities at which to deliver electrical stimulation to the patient. The clinician may determine both minimum and maximum stimulation intensities for efficacious stimulation. Stimulation intensity may be defined by a combination of pulse amplitude and pulse width. The pulse amplitude may be a voltage amplitude or a current amplitude. In some examples, the determined stimulation intensities may be used by programmer 30 to determine stimulation parameters for a plurality of stimulation programs. Each of the plurality of stimulation programs may be associated with a different patterned pulse. The patterned pulses may each be associated with a different sensation perceived by patient 12 in response to the applied stimulation. In some examples, a user may adjust one or more parameters of a stimulation therapy program either directly or indirectly. The adjustments to the stimulation parameters may be limited by the maximum and minimum stimulation intensities determined during initial programming.

System 10 is one example of a system that facilitates programming the intensity of the electrical stimulation therapy based on electrical charge. Using programmer 30, a user may select one or more desired stimulation sensations. Based on the selected stimulation sensation, the programmer may select an initial stimulation therapy program. The initial stimulation therapy program may include stimulation therapy parameters determined during, or based upon, the initial programming. Using programmer 30, a user may adjust one or more stimulation characteristics for a given program, or select a particular stimulation program for electrical stimulation therapy. Programmer 30 may adjust at least one stimulation parameters of the therapy program in conjunction with the adjustment entered by the user. For example, a user may select a parameter(s) to induce an increase in the pressure felt from the stimulation. Programmer 30 may adjust the amplitude and/or pulse width of the stimulation therapy in order to provide a feeling of increased pressure to the patient. The adjustments to the stimulation therapy program parameters in response to an adjustment to a stimulation characteristic may be limited by one or more thresholds of stimulation parameters determined during initial programming FIG. 2 is a block diagram illustrating an example implementation of IMD 20 of FIG. 1. In the example of FIG. 2, IMD 20 includes a processor 22, memory 24, stimulation generator 26, telemetry module or circuitry 28, at least one sensor 31 and power source 32. As shown in FIG. 2, stimulation generator 26 is coupled to leads 16. Each of leads 16A and 16 respectively comprises electrodes 21A-21D and 21E-21H (collectively "electrodes 21").

Processor 22 controls stimulation generator 26 to deliver electrical stimulation therapy according to stimulation parameters, e.g., therapy programs, stored in memory 24 and/or received from programmer 30 via telemetry module 28. In some cases, stimulation parameter values received from programmer 30 are commands to modify, e.g., increment or decrement, one or more stimulation parameter values, such as pulse width or pulse amplitude. In some examples, processor 22 with stimulation generator 26 provides stimulation to electrodes 21 in the form of electrical current or voltage pulses. Stimulation generator 26 may utilize, under the control of processor 22, any combination or configuration of electrodes 21 on leads 16.

Processor 22 may comprise any one or more of a microprocessor, digital signal processor (DSP), application specific integrated circuit (ASIC), field-programmable gate array (FPGA), or other digital logic circuitry. Memory 24 stores instructions for execution by processor 22 e.g., instructions that when executed by processor 22 cause the processor and IMD 20 to provide the functionality ascribed to them herein. Memory 24 may include any one or more of a random access memory (RAM), read-only memory (ROM), electronically-erasable programmable ROM (EEPROM), flash memory, or the like. The functions attributed to processor 22 herein may be embodied as hardware, firmware, software, or the like.

Telemetry module or circuitry 28 may include circuitry for facilitating wireless telemetry, e.g., via radio frequency (RF) communication or proximal inductive interaction with similar circuitry within external programmer 30. Power source 32 delivers operating power to the components of IMD 20. Power source 32 may include a battery and a power generation circuit to produce the operating power. In some examples, the battery may be rechargeable to allow extended operation. Recharging may be accomplished through proximal inductive interaction between an external charger and an inductive charging coil within IMD 20. In other examples, non-rechargeable batteries may be used. As a further alternative, an external power supply could transcutaneously power IMD 20 whenever stimulation is needed or desired.

In the illustrated example, memory 24 stores predetermined function 23 relating a characteristic of a sensation to one or more stimulation parameters. In some examples, processor 22 controls stimulation generator 26 to adjust the pulse amplitude and pulse width of the stimulation pulses delivered by the generator according to function, i.e., in order to maintain or substantially maintain the overall sensation while adjusting a particular characteristic of function 23. Processor 22 may adjust one or more stimulation parameters in response to commands to modify, e.g., increment or decrement, a stimulation sensation characteristic, such as perceived intensity, from programmer 30 received via telemetry module 28, or based on instructions to modify a stimulation characteristic stored in memory 24, e.g., at a time or after an interval according to a schedule, or in response to some condition sensed via electrodes 21 or another sensor. In examples where the characteristic of the stimulation is perceived intensity, processor 22 may control stimulation generator 26 to increase or decrease both amplitude and pulse width at substantially the same time to maintain the sensation, or may alternate between adjustments to pulse amplitude and width to substantially maintain the sensation.

Figure 3:
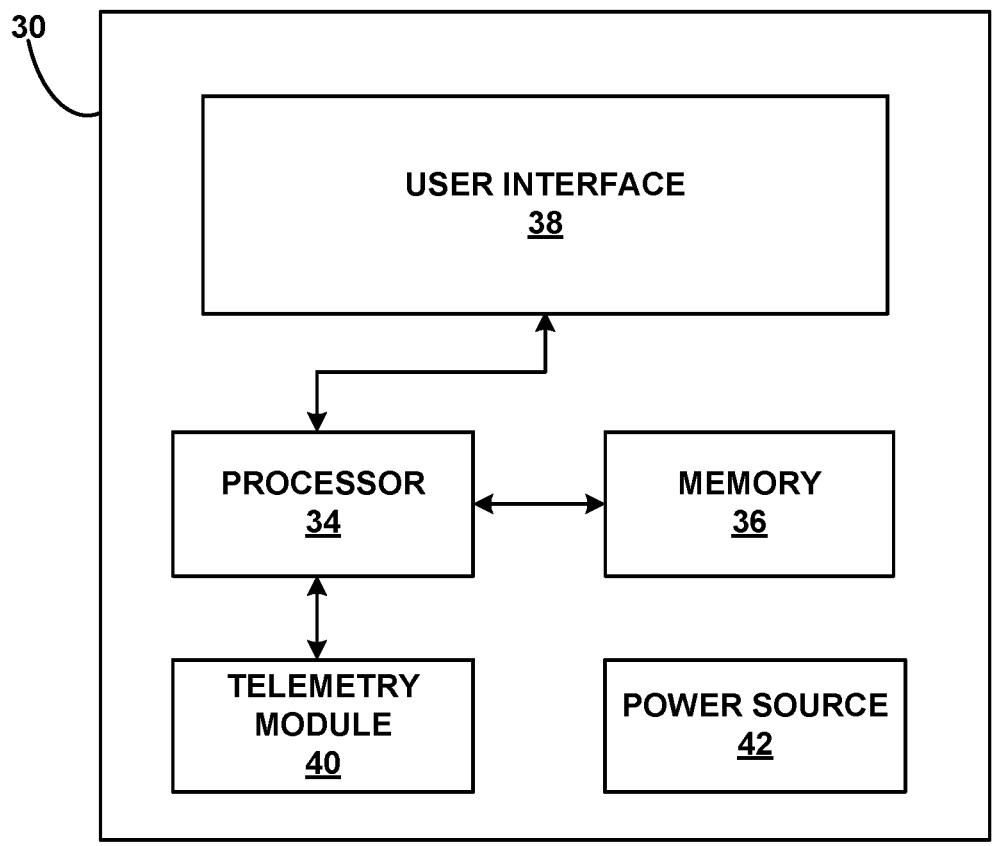
FIG. 3 is a block diagram illustrating an example configuration of an external programming device for programming and controlling the implantable medical device of FIG. 2.

For example, a user such as patient 12 may select a desired stimulation sensation via a user interface of a programmer (FIG. 3). IMD 20 may receive the selected stimulation sensation via telemetry module 28. Based on the selected stimulation, processor 22 may generate a stimulation therapy program or select and retrieve a stored stimulation therapy program from memory 24. Each stimulation sensation may be associated with one or more stimulation sensation characteristics. Example stimulation sensation characteristic may include perceived intensity of sensation; vibration, pulse or tapping frequency; vibration, pulse or tapping pattern; location of sensation; pattern of moving touch, or area of sensation. A user may have one or more stimulation sensation characteristics to modify.

In the illustrated example, memory 24 also stores therapy programs 25. Therapy program 25 comprises a plurality of therapy programs, each program associated with a sensation. For example, memory 24 may store a program providing electrical stimulation resulting in a sensation of constant pressure, a program providing electrical stimulation resulting in a sensation of pulsing pressure, a program providing electrical stimulation resulting in a sensation of vibration, a program providing electrical stimulation resulting in a sensation of tapping, and a program providing electrical stimulation resulting in a sensation of moving touch, for example. In some examples, the therapy programs may include initial therapy parameters values set during the initial programming of system 10. Function 23 may include instructions for adjusting the therapy parameter values of therapy programs 25 in order to adjust one or more characteristics of a sensation while still maintaining the sensation. For example, function 23 may include instructions of how to adjust one or more therapy parameter values in order to increase perceived intensity associated with the sensation. In other examples, function 23 may include instructions of how to adjust one or more therapy parameter values in order to increase a rate of tapping, vibration, or pulsing associated with a particular sensation. For example, function 23 may include a predefined ratio of pulse width to amplitude at which changes to a program are made in order to increase perceived intensity. The ratio may be selected to maintain the pulse width to amplitude ratio at or near a desired spot on the knee of a strength duration curve as the intensity of the stimulation changes. In some examples, function 23 may be stored in memory 36 of programmer 30 (FIG. 3). One or more of the instructions in function 23 may executed by either IMD 20 or Programmer 30.

In some examples, changes to one or more stimulation parameters for a therapy program may be made based on a detected change in posture. The posture of the patient may be detected using sensor 31 when realized as a three-axis accelerometer for example. The change in intensity based on a change in posture may be made in order to maintain the sensation felt by patient 12. A change in intensity may be necessary to maintain a sensation in response to posture as one or more of the electrodes 21 may change position with respect to target nerve tissue with a change in patient posture.

FIG. 3 is a functional block diagram of an example configuration of programmer 30. In the example of FIG. 3, external programmer 30 includes a processor 34, memory 36, user interface 38, and telemetry module 40, and power source 42. Processor 34 processes instructions from memory 36 and controls the various components of programmer 30 to provide the functionality ascribed to the programmer herein. Processor 34 may comprise any one or more of a microprocessor, digital signal processor (DSP), application specific integrated circuit (ASIC), field-programmable gate array (FPGA), or other digital logic circuitry. The functions ascribed to processor 34 herein may be embodied as hardware, firmware, software, or any combination thereof. Memory 36 stores the instructions executed by processor 34. Memory 36 may include any one or more of a random access memory (RAM), read-only memory (ROM), electronically-erasable programmable ROM (EEPROM), flash memory, or the like.

A user, either a clinician or patient 12, may interact with processor 34 through user interface 38. Any of the user interfaces described herein may be an example of or provided by user interface 38, such as graphical user interfaces 100 and 112 of FIGS. 5 and 6. User interface 38 may include a display, such as a liquid crystal display (LCD), light-emitting diode (LED) display, or other screen, to show information related to stimulation therapy, and buttons or a pad to provide input to programmer 30. User interface 38 may also comprise input media such as buttons, soft keys, a pointing device, i.e., a mouse, a trackball, a scroll wheel, a pointstick, or a touchpad. In some examples, the display may be a touch screen that enables the user to select options directly from the display screen, e.g., with a stylus.

Wireless telemetry between IMD 20 and programmer 30 may be accomplished by radio frequency (RF) communication or proximal inductive interaction. This wireless communication is possible through the use of telemetry module 40. Accordingly, telemetry module 40 may include circuitry for such communication. In some examples, telemetry module 40 further comprises a wired or wireless network interface for communication with a computer network, e.g., with a server or database, for transmitting data and/or receiving commands. Power source 42 may include a battery. Power source 42 may rechargeable or non-rechargeable. In some examples, programmer 30 includes a port through which power source 42 may be recharged.

Processor 34 may receive one or more therapy programs 25 from IMD 20 via telemetry module 40, and store the therapy programs 25 in memory 36. In other examples, memory 36 may be programmed, or loaded, during manufacture or at some other time, with therapy programs 25 for IMD 20. As described in greater detail below, processor 34 may automatically adjust one or more therapy parameters based on input received from user interface 38. Processor 34 may provide commands to control IMD 20 to modify the parameters of stimulation via telemetry module 40 in response to the user-input. In other examples, processor 34 may relay the user-input to processor 22 of IMD 20 via telemetry modules 28 and 40. In some examples, one or more changes to therapy parameters may be based on a pre-determined schedule. The changes to the therapy parameter values may be part of a predetermined therapy program.

For example, memory 36 may include function 23 and stored therapy programs 25 (as shown in FIG. 2). Processor 34 may execute one or more of the instructions from function 23 in order to adjust one or more of the stimulation therapy parameters in response to user input of an adjustment to a stimulation sensation. The adjusted stimulation therapy parameters may be provided to IMD 20 via telemetry modules 28 and 40. In addition, the adjusted stimulation therapy parameters may be stored in either (or both) of memory 36 and memory 24. In some examples, processor 34 may retrieve a set of stimulation therapy parameters from therapy program 25 of memory 36 based on a sensation selection made via user interface 38. The retrieved therapy program or set of stimulation therapy parameters may then be provided to IMD 20 via telemetry modules 28 and 40.

Figure 4:
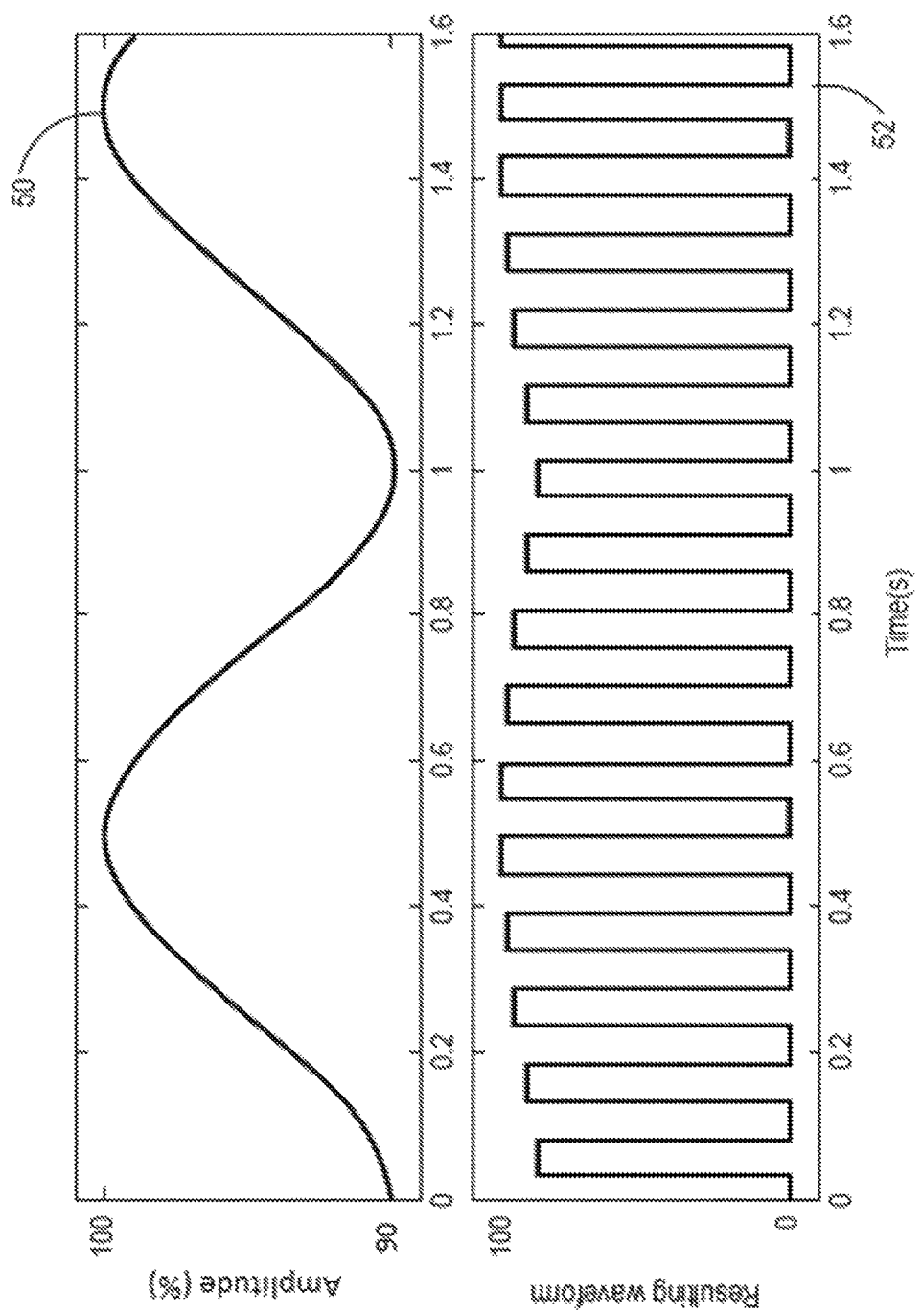
FIG. 4 is an example waveform associated with a stimulation pattern having a therapeutic effect and providing a particular sensation to a patient.

FIG. 4 is an example waveform associated with a stimulation pattern having a therapeutic effect and providing a particular sensation to a patient. As shown in FIG. 4, the pulse width of waveform 52 varies according to a sine wave 50. The variation in pulse width according to waveform 52 may result in a stimulation sensation such as a pulsing pressure. The sine wave 50 has a frequency of 1 Hz. This results in a cycling from a maximum pulse width in the therapy program to the minimum pulse width within the therapy program and back to the maximum pulse width every second. The pulse width of waveform 52 varies between a maximum frequency pulse width and a minimum frequency pulse width. In some examples, the amount of oscillation or variation in pulse of width of sine wave 50 may be set at a percentage of the maximum frequency pulse width. For example, if the maximum pulse width is 300 microseconds (µs), and the pulse width modulation is 10% of the maximum pulse width, then the pulse width may vary between a pulse width corresponding to a pulse width of 270 microseconds and a pulse width corresponding to 300 microseconds. Although the overall intensity of stimulation may be approximately equal to a steady pulse at 285 microseconds, the stimulation sensation resulting from the oscillating pulses differs. In some examples, the amplitude of stimulation may stay the same for each pulse, and in other examples, the amplitude may be adjusted with each pulse width in order to maintain the same level of overall intensity for each stimulation pulse.

In other examples, the pulse width is varied according to another predetermined pattern or waveform. The predetermined pattern or waveform is a modulation envelope. For example, the pulse widths may vary according to a square wave, a triangle wave, a sawtooth wave, a wave changing in a logarithmic pattern over a modulation period, or a wave changing in an exponential pattern over the modulation period. The modulation envelope may have a pattern repeat period. The period of pattern repeat may be a modulation frequency. For example, if the modulation frequency is 1 Hz, then the modulation envelope pattern repeats every second. In each example, the pulse width varies from a minimum pulse width to a maximum pulse width according to the amplitude of the waveform. The minimum amplitude of the waveform corresponds to the minimum pulse width and the maximum amplitude of the waveform corresponds to a maximum pulse width. The minimum and maximum values of pulse width may be determined based on a third value. For example, the waveform may vary the pulse width a certain percentage above and below the third value. In some examples, the third value may be provided via user input. In some examples, the stimulation amplitude for each pulse also varies in order to maintain a pulse intensity. The pulse intensity may be defined by the pulse width multiplied by the pulse amplitude. The modulation of pulse widths based on each different waveform results in a different stimulation sensation.

The modulation of stimulation therapy parameters based on a modulation envelope may result in a particular sensation depending upon the shape of the modulation envelope. For example, stimulation modulated according to a sine wave modulation envelope results in different patient sensation than stimulation modulated according to a sawtooth wave modulation envelope. In some examples, the modulation envelope may be used to generate a template therapy program. Personalized therapy parameter values within the template program may be determined during initial programming. In addition, the stimulation therapy parameter values may be further adjusted based on user adjustments to one or more stimulation characteristics during application of stimulation.

In examples, the creating of a particular sensation may include modifying the therapy parameter of which electrode or electrode pair is providing stimulation. For example, for the stimulation sensation of moving touch, the application of electrical stimulation between different electrode pairs. In some examples, the locations may change according to a predefined pattern. In other examples, a desired sensation may be achieved by changing between electrode pairs at random intervals or in a random order.

In some examples, the pulse amplitude may vary according to sine wave 50. The variation in pulse amplitude according to waveform 52 may result in a stimulation sensation such as a pulsing pressure. The sine wave 50 has a frequency of 1 Hz. This results in a cycling form a maximum pulse amplitude in the therapy program to the minimum pulse amplitude within the therapy program and back to the maximum pulse amplitude every second. The pulse amplitude varies between a maximum pulse amplitude and a minimum pulse width amplitude. The maximum and minimum pulse amplitudes may be set by a user. In some examples the minimum pulse amplitude may be the minimum amplitude needed to achieve capture of a target nerve and the maximum amplitude may be just below a threshold amplitude resulting in a painful sensation. In some examples, the amount of oscillation or variation in pulse width of sine wave 50 may be set at a percentage of the maximum pulse voltage amplitude or pulse current amplitude. For example, if the maximum pulse voltage amplitude is approximately 5 V, and the pulse voltage amplitude modulation is 10% of the maximum pulse voltage amplitude, then the pulse amplitude may vary between a pulse amplitude corresponding approximately 4.5 V to approximately 5 V. Although the overall intensity of the stimulation may be approximately equal to a steady pulse at 4.5 V, the stimulation sensation resulting from the oscillating pulse differs. In some examples, the pulse width may stay the same for each pulse, and in other examples the pulse width may be adjusted with each pulse amplitude in order to maintain the same level of overall intensity for each stimulation pulse. In another example, the pulse current amplitude may be modulated based on sine wave 50. For example, if the maximum pulse current amplitude is approximately 5 mA, and the pulse current amplitude modulation is 10% of the maximum pulse current amplitude, then the pulse amplitude may vary between a pulse amplitude corresponding to approximately 4.5 mA to approximately 5 mA.

In other examples, the pulse amplitude is varied according to another predetermined pattern or waveform. The predetermined pattern or waveform is a modulation envelope. For example, the pulse amplitude may vary according to a square wave, a triangle wave, or a sawtooth wave. In each example, the pulse amplitude varies from a minimum pulse amplitude to a maximum pulse amplitude according to the amplitude of the waveform. The minimum amplitude of the waveform corresponds to the minimum pulse amplitude and the maximum pulse amplitude corresponds to a maximum pulse amplitude. The minimum and maximum values of pulse amplitude based on a third value. For example, the waveform may vary the pulse amplitude a certain percentage above and below the third value. In some examples, the third value may be provided via user input. In some examples, the stimulation pulse width for each pulse also varies in order to maintain a pulse intensity. The modulation of pulse amplitudes based on each different waveform results in a different stimulation sensation. In addition, modulating a pulse width according to a modulation envelope such as sine wave 50 may provide a stimulation sensation that is different than the stimulation sensation provided by modulating a pulse amplitude according to the same modulation envelope such as sine wave 50.

In some examples, the charge per pulse may be modulated according to the modulation envelope. For example, both pulse amplitude and pulse width may be modulated according to the modulation envelope. In other examples, one of the pulse amplitude or pulse width is modulated according to the modulation envelope while the other of pulse width or pulse amplitude is held at a constant value.

Figure 5:
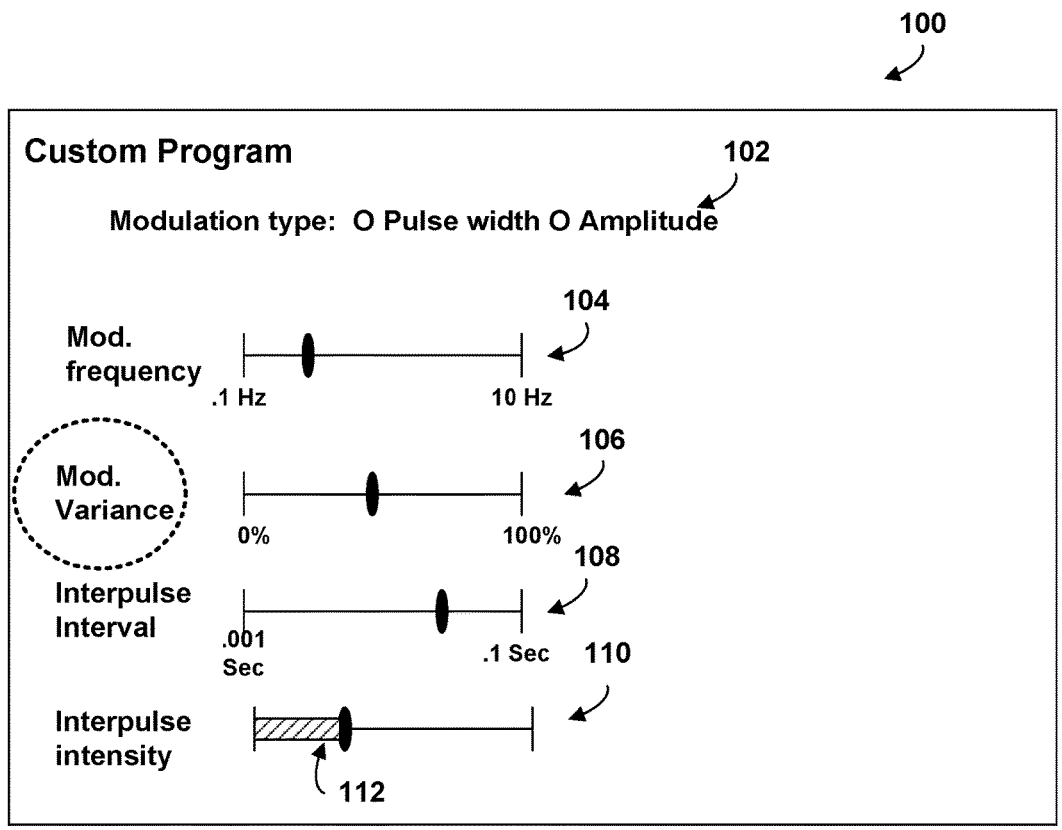
FIG. 5 is a conceptual diagram of a user interface which may be displayed by a user interface of the programmer of FIG. 3.

FIG. 5 is a conceptual diagram of a user interface 100 which may be displayed on user interface 38 of programmer 30 (FIG. 3). User interface 38 of programmer 30 provides a human-machine interface for a user such as a patient or clinician to make selections or adjustments to a therapy program to result in stimulation sensation. User interface 100 illustrates an example of selections for a custom stimulation program. The user may either create a new custom stimulation sensation program, or make adjustments to a previously generated custom stimulation sensation program. The user may select a modulation type 102. For example, a user may select modulation of pulse width or of pulse amplitude. Based on the selection of modulation type 102, the therapy parameter values of either pulse width (for a pulse width modulation type) or pulse amplitude (for a pulse amplitude modulation type) are modulated according to other parameters selected by the user, such as modulation frequency and modulation variance. A user may select a modulation frequency 104. The modulation frequency may range from approximately 0.1 Hz to approximately 10 Hz. The modulation frequency of the repeating pulse indicates the length of the modulation envelope. For example, modulation frequency corresponds to the frequency of the sine wave 50 in FIG. 3. The user may also select a modulation variance 106. The modulation variance 106 represents how much the pulse width or amplitude varies within a modulation envelope. For example, if the modulation variance 106 is set to 50% then either the pulse width or amplitude (depending upon selection of modulation type) will vary from the maximum pulse width to 50% of the maximum pulse width and back again in a pattern determined by the modulation envelope.

The interpulse interval 108 sets the time between pulses (frequency of pulses). Interpulse intensity 110 may set a value for intensity which is a combination of pulse width and amplitude. In some examples, status bar 112 indicates the actual current intensity of the pulses as stimulation generator 26 ramps the intensity up to the desired intensity at the beginning of the program. Although inputs for modulation frequency 104, modulation variance 106, interpulse interval 108, and interpulse intensity 110 are shown as sliding scales, user interface 110 may display the various components of the custom program in other ways. For example, a user may be able to type in desired value for each component, use physical or graphical dials, press-and-hold or other touch screen gestures, select from a pick list, or verbally communicate the value. In addition, custom program options may include selection of modulation envelope shape, and maximum amplitude or pulse width.

Based on the information input by a user via user interface 100, processor 34 (or processor 22) generates a therapy program. The therapy program includes stimulation parameters include the pulse width and pulse amplitude for each stimulation pulse which varies according to the modulation requirements. Processor 34 determines the appropriate pulse amplitude (or pulse width) in order to maintain the desired intensity level.

Figure 6:
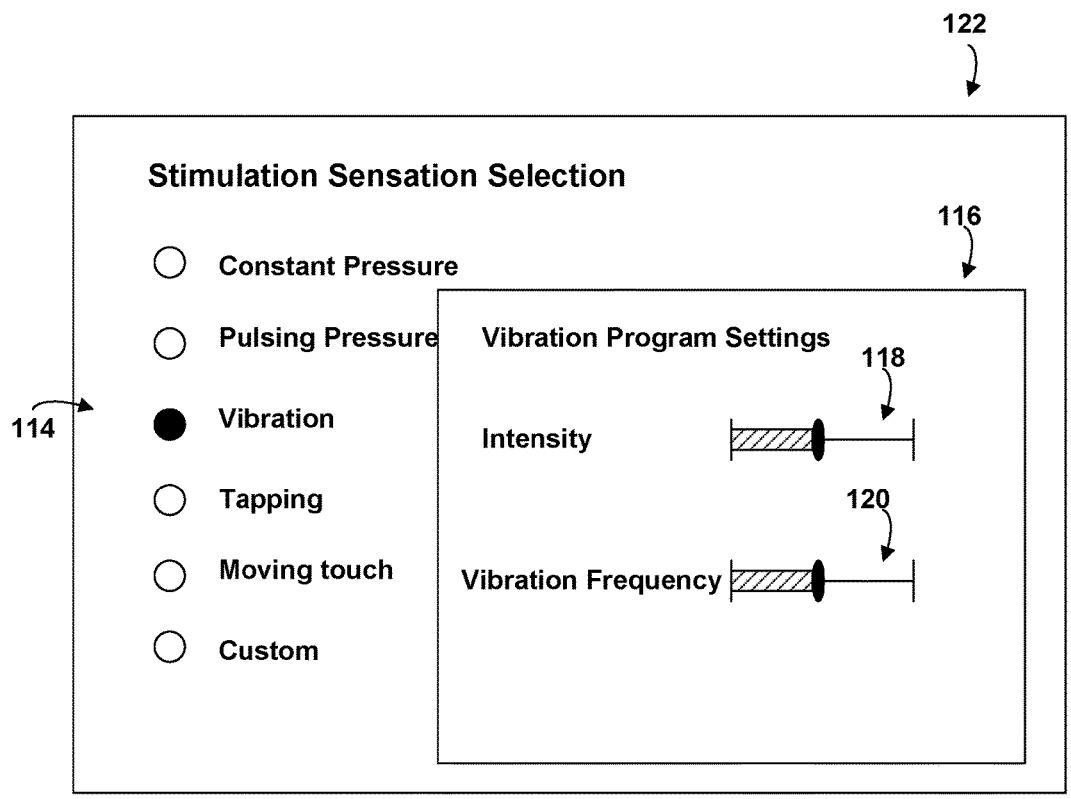
FIG. 6 is another conceptual diagram of a user interface which may be displayed on a user interface of the programmer of FIG. 3.

In some examples, user interface 100 may allow a user to save a custom program, and name the custom program. For example, the user may adjust various settings until a desired sensation, such as "tingling" is achieved. The user may then save the custom program in order to use the program in the future without needing to recreate the program. Multiple custom programs may be generated in this manner. As shown in FIG. 6, (discussed below) one or more custom or predefined programs associated with a particular sensation may be displayed to a user in order to allow the user to select between various stimulation sensations.

FIG. 6 is a conceptual diagram of a user interface 122 which may be displayed on user interface 38 of programmer 30 (FIG. 3). User interface 122 allows a user to select a stimulation sensation 114. User interface 122 may include a program settings menu 116 for a selected sensation. In some examples, program settings menu 116 opens as a separate screen, such as user interface 100. As shown in FIG. 6, program settings menu 116 may limit a user to adjusting one or more characteristics of the selected sensation program. For example, for a vibration sensation, the user may be able to adjust the perceived intensity of the vibration 118, as well as the frequency of the vibration 120. In other examples, such as a moving touch sensation, the user may be able to select an area the touch sensation moves over, as a characteristic, and/or a pattern of touch such as circular (e.g., clockwise or counter-clockwise) or linear (e.g., left to right). For a constant pressure sensation, the characteristics may include the perceived intensity of the pressure. For a pulsing pressure sensation, the characteristics may include the perceived intensity of the pressure, the rate of pulsation, and/or the variation in strength during the pulsing. For a tapping sensation, the characteristics may include the perceived intensity of the tapping, the frequency of the tapping, and the length of each tap, for example. As shown, the sensation may be adjusted along a sliding scale. In some examples, a user may be able to select between predetermined adjustments. For example, the user may be able to select low, medium or high perceived intensity. Stimulation provided to generate a low perceived intensity may be provided at a stimulation intensity equal to a stimulation intensity value approximately 10% above a stimulation intensity perception threshold determined during initial programming. Stimulation provided to generate a high perceived intensity may be provided at a stimulation intensity equal to a stimulation intensity approximately 10% below a stimulation intensity pain threshold determined during initial programming. Stimulation provided to generate a medium perceived intensity may be provided at a stimulation intensity equal to a stimulation intensity value approximately equidistant from the stimulation intensity perception threshold and the stimulation intensity pain threshold.

Based on the user selection of a stimulation sensation, processor 34 may select a therapy program which provides the selected stimulation. Processor 34 may adjust one or more of the therapy parameters based on modifications to one or more of the stimulation sensation characteristics. For example, the processor may adjust a pulse amplitude, pulse width, or combination of pulse amplitude and pulse width in order to adjust a perceived intensity. For some sensations, this may include making amplitude adjustments of different values for each of a variety of pulse widths for programs which vary pulse width in order to achieve a particular sensation. For a change in stimulation area, the processor may adjust which electrodes between which electrical stimulation is provided.

In some examples, the adjusted stimulation parameters may be saved in memory 24 or memory 36. The adjusted stimulation parameters may be saved in association with a predetermined stimulation sensation. For example, an adjusted stimulation program may replace the previous program associated with the sensation of vibration. The next time a user selects the vibration sensation, processor 22 may retrieve the adjusted vibration program from therapy programs 25 and provide stimulation according to the adjusted therapy program stimulation parameters.

Figure 7:
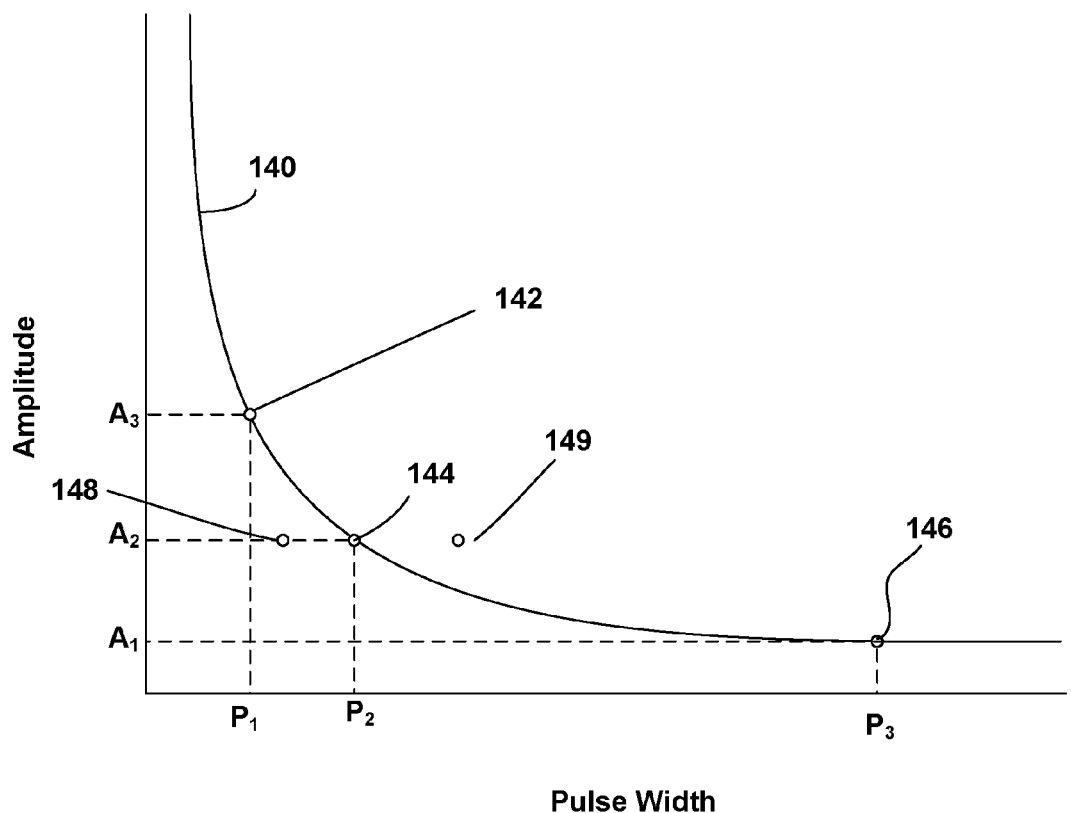
FIG. 7 is a graph illustrating an example strength-duration curve showing perceived stimulation intensity as a function of stimulation pulse amplitude and pulse width.

FIG. 7 is a diagram illustrating an example strength-duration curve 140. Generally, all points along curve 140 define paired pulse width and amplitude values that have substantially equal intensity in the sense that they have a substantially equal ability to activate target neural tissue. The strength duration curve 140 may be used by or included in function 23 to allow processor 22 to create a stimulation program where each individual pulse has a different width, but a substantially equal intensity. For example, a stimulation pulse having a pulse width of $P_1$ and an amplitude of $A_3$, i.e., point 142 on curve 140, a stimulation pulse having a pulse width of $P_2$ and an amplitude of $A_2$, i.e., point 144, and a stimulation pulse having a pulse width of $P_3$ and an amplitude of $A_1$, i.e., point 146, may have substantially equal intensity and a substantially equal ability to capture target neural tissue. The equal intensity and ability to capture neural tissue may result in a substantially equal perceived intensity. In this manner, points 142, 144, 146 define three pulse width and amplitude value pairs, i.e., paired pulse width and amplitude values, which may correspond to a single stimulation intensity. Processor 34 or processor 22 may use strength duration curve 140 to determine an appropriate amplitude A for each pulse width P as pulse width P varies according to a modulation envelope in order to maintain a stimulation intensity. This allows for a substantially uniform perceived intensity while also creating a variety of sensations based on the modulation of the pulse width.

Curve 140 may be a strength-duration curve specific to target neural tissue. Stimulation pulses with pulse amplitude and width pairs along curve, e.g., at points 142, 144 and 146, may have just sufficient intensity to activate the target neural tissue. The strength duration curve may be determined during initial programming of system 10. Stimulation pulses with pulse amplitude and width pairs above the curve, e.g., with the pair defined by point 149, also activate the target tissue. Stimulation pulses with pulse amplitude and width pairs below the curve, e.g., with the pair defined by point 148, will be of insufficient intensity to activate the target tissue. Curve 140 may be empirically determined for the target neural tissue. Points 148 and 149 represent different intensities, and why the amplitude of the pulse may need to be changed during the modulation of the pulse width. For example, points 144, 148, and 149 all correspond to a pulse amplitude $A_2$. However, only pulse widths with values of P2 (point 144) and above (149) result in a stimulation intensity which provides nerve capture, and therefore a sensation for the patient. Accordingly, a change to one or the other of pulse width or pulse amplitude without a corresponding change in the other parameter may result in a change in perceived intensity, including the possibility of failing to provide the desired sensation.

As illustrated by curve 140, there may be a minimum pulse width that is required to activate a target tissue. In general, if a stimulation pulse has a pulse width that is less than this minimum pulse width, the stimulation pulse will likely by unable to activate the tissue no matter how much the amplitude is increased. Similarly, there may be a minimum amplitude along curve 140 that is required to activate a volume of tissue. This minimum amplitude is known as the rheobase amplitude. Additionally, the pulse width value corresponding on curve 140 to twice the rheobase amplitude is known as the chronaxie.

Although all points on curve 140, including 142, 144 and 146, define individual pulse width and amplitude value pairs providing substantially equal stimulation intensity, the individual paired pulse width and amplitude values are not necessarily substantially equal in all other aspects. For example, stimulation sensation can vary depending on the pulse width and amplitude value of the stimulation. The varying of pulse width and amplitude along strength duration curve 140 may provide for an overall changing sensation, such as a pulsing feeling. By maintaining the stimulation intensity along curve 140 while varying pulse width and amplitude parameter values, a stimulation sensation may be provided to a patient 12 with a substantially consistent perceived intensity.

Figure 8:
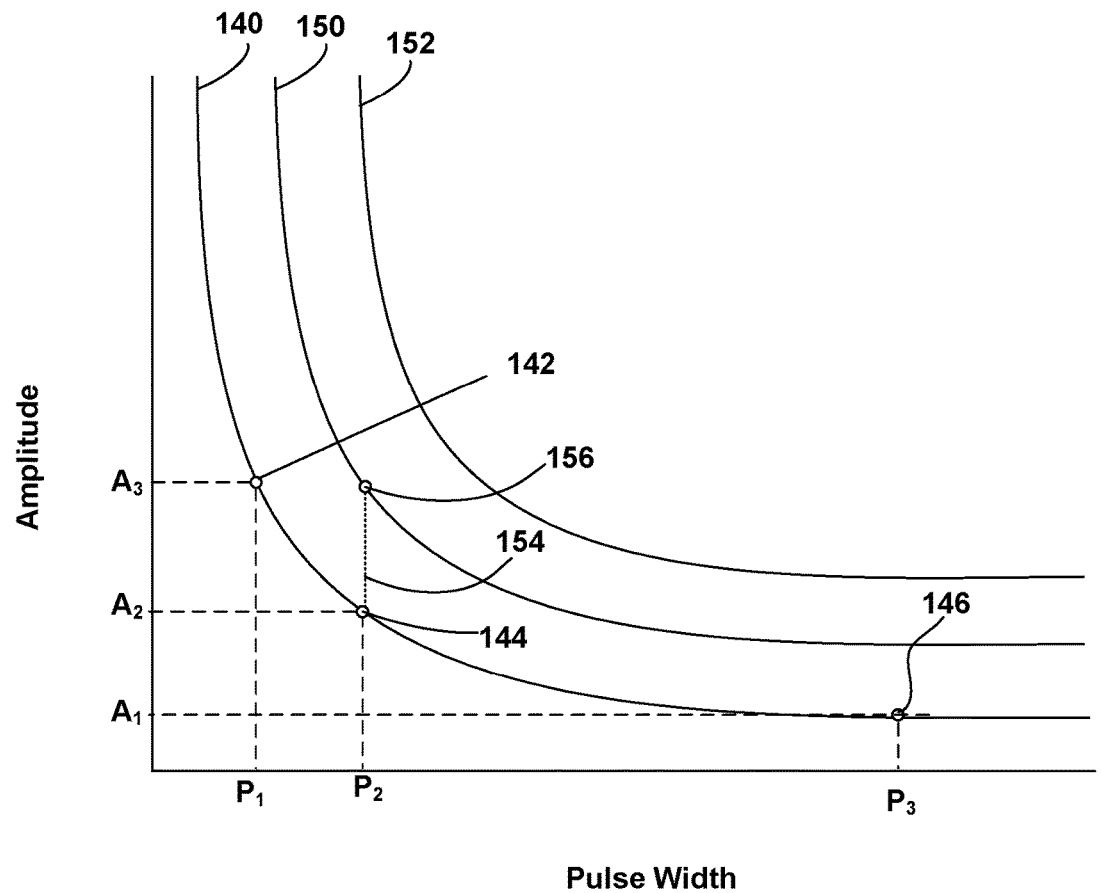
FIG. 8 is a graph illustrating a plurality of strength-duration curves.

FIG. 8 is a diagram illustrating a plurality of strength-duration curves, including curve 140 from FIG. 7, and curves 150 and 152. Curves 150 and 152 may represent strength-duration curves for various selected stimulation intensities. Processor 34 may move from strength duration curve 140 to strength duration curve 150 or 152 based on input from a user adjusting a stimulation characteristic such as perceived intensity. For example, if the user increases the perceived stimulation intensity from strength-duration curve 140 to curve 150, processor 34 may increase the amplitude of stimulation for each pulse with a pulse width of $P_2$ from $A_2$ to $A_3$. The increasing amplitude is represented by line 154, and the desired effect would be perceived when, as an example, pulse amplitude reached A3, i.e., point 156 on curve 150. Increasing intensity in this manner changes the ratio between pulse amplitude and pulse width. Function 23 may include one or more strength duration curves such as curves 150 and 152. Processor 34 or processor 22 may use the plurality of strength duration curves to determine stimulation parameter values in response to an adjustment to one or more stimulation sensations. For example, because the ratio between pulse width and pulse amplitude does not change in a 1 to 1 manner, an incremental change to perceived intensity does not result in a simple change by the same incremental amount to the amplitude of each pulse. Curves 150 and 152 allow processor 34 to calculate all new stimulation parameter values for each pulse in order to maintain a selected sensation while adjusting one or more characteristics of that sensation, such as perceived intensity.

Figure 9:
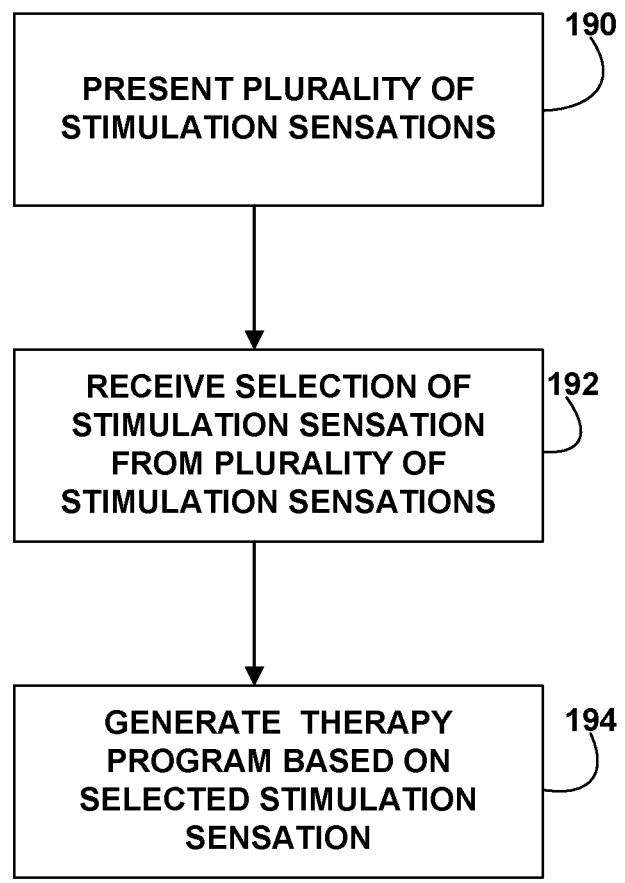
FIG. 9 is a flow chart illustrating an example method consistent with the present disclosure.

FIG. 9 is a flow chart illustrating an example method consistent with the present disclosure. With reference to FIG. 1, programmer 30 presents a user, such as patient 12 or a clinician, a plurality of stimulation sensations (190). The plurality of stimulation sensations may include a variety of different sensations that may be experienced as a result of the delivery of stimulation, such as a constant pressure sensation, a pulsing pressure sensation, a vibration sensation, a tapping sensation, a moving touch sensation, or other types of sensations, as discussed above in connection with at least FIG. 2. The user may select a desired stimulation sensation from the plurality of stimulation sensations, and programmer 30 receives the selection of the stimulation sensation form the plurality of stimulation sensations (192) via user interface 38. Processor 34 generates a therapy program based on the selected stimulation sensation (194). In some examples, generation of the therapy program may include retrieving a previously stored therapy program template from memory 36. Memory 36 may include a plurality of therapy program templates, each associated with a different one of the plurality of stimulation sensations. In this example, one or more of the plurality of therapy program templates may include one or more therapy parameters values selected based upon experimental results shown to have provided a particular sensation (e.g., constant or pulsing pressure, etc.) for a range or spectrum of patients having a same or similar ailment, condition, or anatomy. In some examples, two or more templates may be associated with each particular sensation, and it is contemplated that when a first template for a selected sensation does not provide the selected sensation, one or more therapy parameter values may be adjusted, or another template associated with the sensation may be selected to determine if the desired sensation is realized based on therapy parameter values defined within or by the another template.

In some examples, such as during initial programming of the device, stimulation may be provided by IMD 20 according to the therapy parameters values of the therapy program template. The user may adjust one or more characteristics of the stimulation sensation during initial programming. In response to the adjustment of the stimulation sensation, processor 34 may adjust one or more of the stimulation parameters associated with the therapy program template. For example, a user may not feel the selected sensation when therapy is provided according to the stimulation therapy parameters associated with the therapy program template. The user may increase the stimulation intensity until the selected sensation is felt. In response to the user input of an increase in stimulation intensity, processor 34 may adjust one or more of the therapy parameter values while maintaining an overall stimulation therapy program that provides the selected stimulation sensation. For example, the processor may increase the stimulation amplitude while maintaining pulse width in order to increase the perceived intensity of the stimulation. The adjusted therapy parameter values may be stored as a personalized therapy program providing the selected stimulation sensation.

Figure 10:
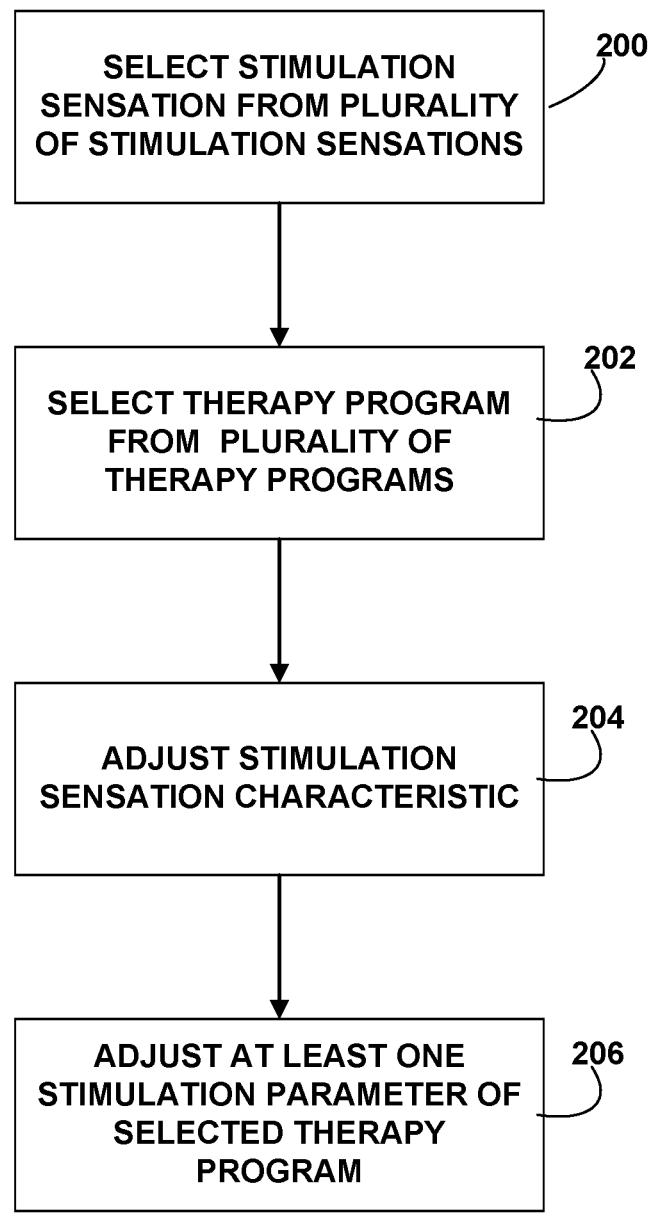
FIG. 10 is flow chart illustrating an example method consistent with this disclosure.

FIG. 10 is a flow diagram illustrating an example method consistent with the present disclosure. With reference to FIGS. 1-3, a user, such as patient 12 or a clinician, enters user input selecting a stimulation sensation from a plurality of stimulation sensations. In response, processor 34 or 22 selects the stimulation sensation from the plurality of stimulation sensations (200). The selection may be made via user interface 38 which displays the plurality of stimulation sensations. In response to the selection, processor 34 or processor 22 selects a therapy program from a plurality of therapy programs (202). Although discussed with respect to a therapy program, processor 34 or processor 22 may select a set of therapy parameters from a plurality of sets of therapy parameters. The therapy program may include a plurality of stimulation parameters values which vary over time within the therapy program in order to provide a particular selected stimulation sensation. For example, as shown in FIG. 4, the pulse width may modulate according to a modulation envelope. The therapy program stimulation parameter values may be default values that have been preselected to provide the selected stimulation sensation. In some examples, the default values may be determined during initial programming of system 10. The user may be permitted to enter user input adjusting a stimulation sensation characteristic (204). The user may adjust the intensity of the stimulation, for example. In response to the user adjustment to a stimulation sensation characteristic, processor 34 adjusts one or more stimulation parameters of the selected therapy program (206) to achieve the adjustment to the characteristic. For example, in response to a change in stimulation intensity, processor 34 may adjust the amplitude of each of the different pulses with the therapy program to achieve the desired perceived stimulation intensity. The value of the change in amplitude may be different for each of the different pulse widths. The adjustments to the stimulation parameters may be made based on function 23, for example.

Figure 11:
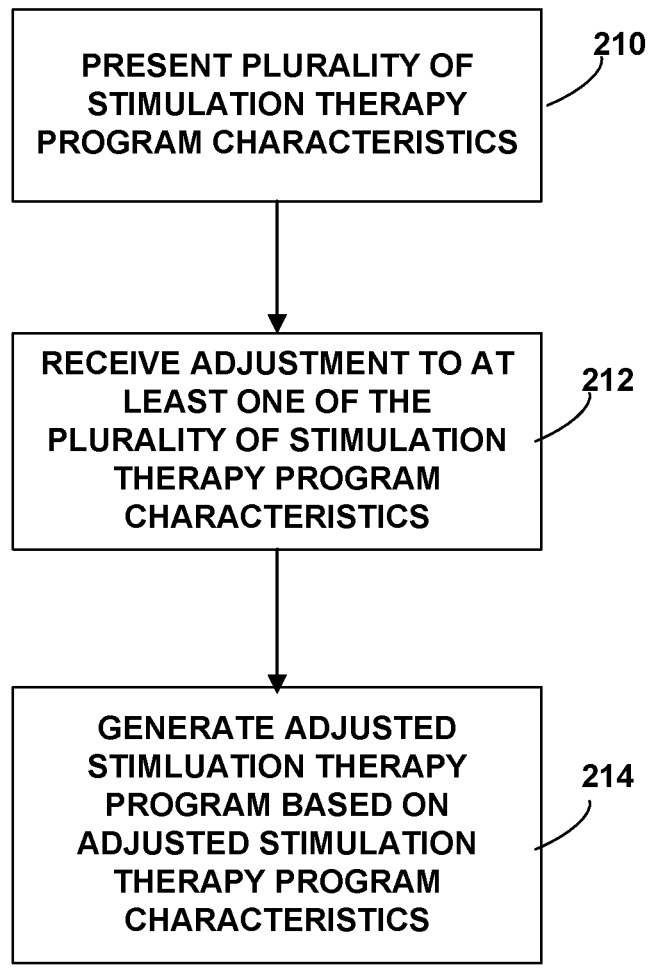
FIG. 11 is a flow chart illustrating an example method consistent with this disclosure.

FIG. 11 is a flow chart illustrating an example method consistent with this disclosure. A user interface presents a plurality of stimulation therapy program characteristics (210) to a user. The stimulation therapy program characteristics may include modulation type, such as pulse width or pulse amplitude, modulation variance, modulation frequency, interpulse interval, intensity, and/or modulation shape, for example. A user interface may receive an adjustment to at least one of the plurality of stimulation therapy program characteristics from a user (212). For example, a user may adjust the modulation frequency associated with the therapy program, and/or the interpulse intensity. The adjustment may be limited by the patient programmer. For example, the patient programmer may not allow a user to increase or decrease the stimulation intensity above or below predetermined ranges. In some examples, the predetermined ranges may be patient specific. In response to the adjustment, processor 34 generates an adjusted stimulation therapy program based on the adjusted stimulation therapy program characteristics (214). The adjusted stimulation therapy program includes at least one stimulation parameter value which is modulated over time. For example, the pulse width and/or pulse amplitude may vary over time. The modulation in stimulation parameters results in a stimulation sensation different from stimulation applied according to constant stimulation therapy parameter values. In some examples, one or more of the adjustments to the stimulation parameters values are made according to a function 23 stored in memory in memory 24 or memory 36. The function may maintain a desired ratio of pulse amplitude and pulse width. In other example, function 23 may constrain the pulse amplitude and pulse width to values which capture the target neural tissue.

In some examples, simulation is provided to patient 12 by IMD 20 according to the adjusted stimulation therapy program. If the desired stimulation sensation is achieved, the stimulation program may be stored in memory 24 or memory 36. If the desired stimulation sensation is not achieved, then the user may make one or more additional adjustments, a new adjusted stimulation program is generated, and stimulation is again delivered based on the updated stimulation therapy program. These steps may be repeated until the desired stimulation sensation is achieved.

Figure 12:
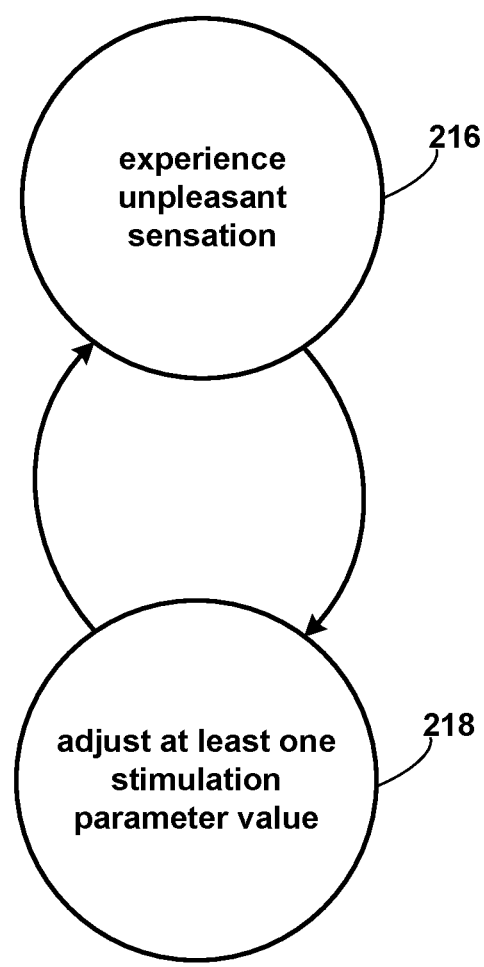
FIG. 12 is a conceptual diagram illustrating a workflow for selecting stimulation parameter values to achieve a desired stimulation sensation.

As mentioned above in connection with FIG. 10, therapy program stimulation parameter values may be default values that have been preselected to provide an intended stimulation sensation. Referring now to FIG. 12, a conceptual diagram is shown to illustrate a workflow, from the perspective of a patient, to dial-in to stimulation parameter values to achieve a desired stimulation sensation. Specifically, the patient may experience (216) an unpleasant sensation as a side-effect of applied electrical simulation, but the patient may then adjust (218) the instant setpoint of one or more therapy stimulation parameters to alleviate the unpleasant sensation. For example, the instant setpoint of the intensity control 118 as shown in FIG. 6 may be such that the patient experiences paresthesia, but the patient may then lower or decrease the setpoint to minimize the unpleasant "pins and needles" sensation. In this example, the minimum intensity setpoint (represented by the lower end of the bounded range of intensity setpoint values as shown in FIG. 6) is greater than a minimum threshold intensity required to provide intended therapeutic effects and thus, while the patient is afforded the opportunity minimize the unpleasant sensation, efficacy of the applied electrical stimulation remains unaffected.

Figure 13:
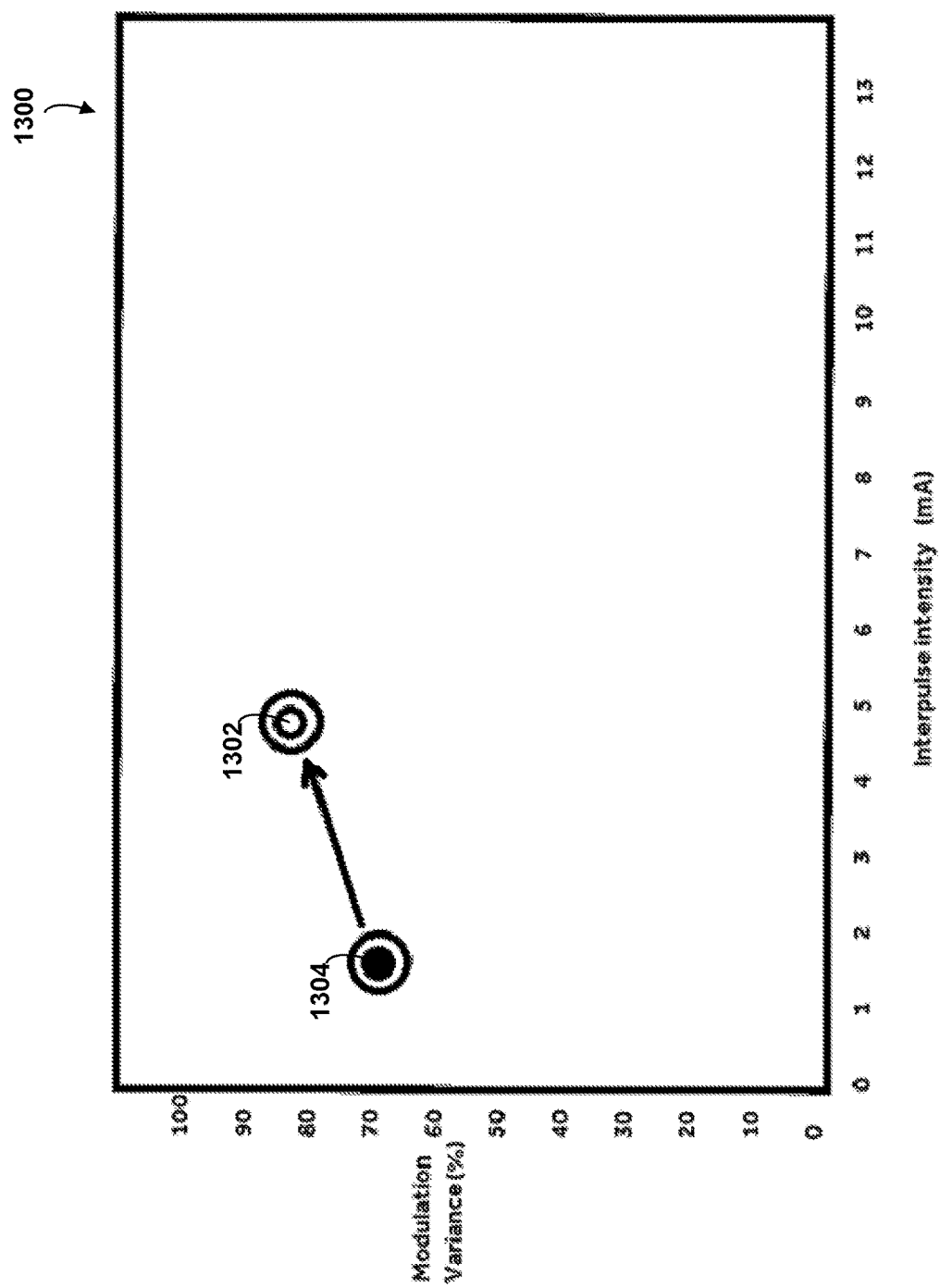
FIG. 13 is a conceptual diagram of a graphical user interface which may be displayed by a user interface of the programmer of FIG. 3.

As discussed above in connection with FIG. 5, it is contemplated that various components of a custom program may be displayed in various ways. For example, in contrast to a sliding scale(s), a user may type in a desired value for each component, use physical or graphical dials, press-and-hold or perform other touch screen gestures, select from a pick list, and/or verbally communicate a value. Referring now to FIG. 13, a multi-dimensional programming aspect is contemplated whereby at least two parameters for electrical stimulation may be adjusted in a "press-hold" and/or "drag-drop" implementation to induce a desired sensation.

More specifically, FIG. 13 illustrates an interface 1300 configured to allow a user, e.g., a patient, to more easily modify two settings to induce an optimal sensation. For example, there is a relationship between the overall amplitude of a waveform and the percent modulation variance of the waveform. In the example of FIG. 13, it is contemplated that a user may press-hold a target area or location 1302 in or within the interface 1300 to select a target modulation variance and amplitude with a single press-hold gesture. In this example, existing settings would transition from the values defined at an initial area or location 1304 to the values defined at the target location 1302. Similarly, a press-drag gesture may be performed where a user may press-hold the initial location 1304 and then drag their finger along a touch screen (within the interface 1300) to the target location 1302 to select a target modulation variance and amplitude with a single press-drag gesture. In some examples, the user may move the target around in real-time, and initial settings would chase or follow the target settings in a relatively smooth and non-invasive manner so that the patient does not experience a sharp or unpleasant sensation during the transition. For example, the value of each setting may gradually transition over a time period following the user input, e.g., ramp up or down, linearly or non-linearly, from the value defined by the initial location 1304 to the value defined by target location 1302. In other examples, the values of the settings may discontinuously transition, e.g., jump instantaneously, from initial to target settings without a smooth transition between initial and target settings.

Further, the target may be mapped directly onto the x- or y-axis of the interface 1300 by a press-hold gesture, and then one-dimensional programming may be performed by moving the setpoint or setting horizontally or vertically along a particular one of the x- or y-axis. Still further, it is contemplated that any parameter as discussed throughout may be "dragged" onto the x- or y-axis, to replace a parameter currently mapped to the corresponding axis, and then adjusted alone (i.e., one-dimensional programming) or together (i.e., two-dimensional programming) with another parameter within the interface 1300 as desired. For example, a user might want to program interpulse intensity with interpulse pulse width at the same time, or modulation variance and interpulse frequency, etc., instead of modulation variance and interpulse intensity as shown in the example of FIG. 13. In this example, the interface 1300 of FIG. 13 may be displayed simultaneously with the user interface 100 of FIG. 5, and then the user could "touch" one of the controls as shown in FIG. 5 (illustrated by intermittent line in FIG. 5) and then drag-drop the selected control onto the x- or y-axis of the interface 1300. Still other user interfaces are contemplated.

For example, a user interface is contemplated that would enable a user to switch between induced sensations on any particular time scale (e.g., seconds, hours, etc.). In other words, a user interface is contemplated that would allow the user to select different times that the different sensations would occur. For example, it could be that a mild pressure sensation is preferred at night, and a stronger pressure sensation is preferred during the day. The sensations however may be switched more frequently, such as every several seconds, and the changes may cause different types of sensations or move the sensation to a different area of the body over time.

Figure 14:
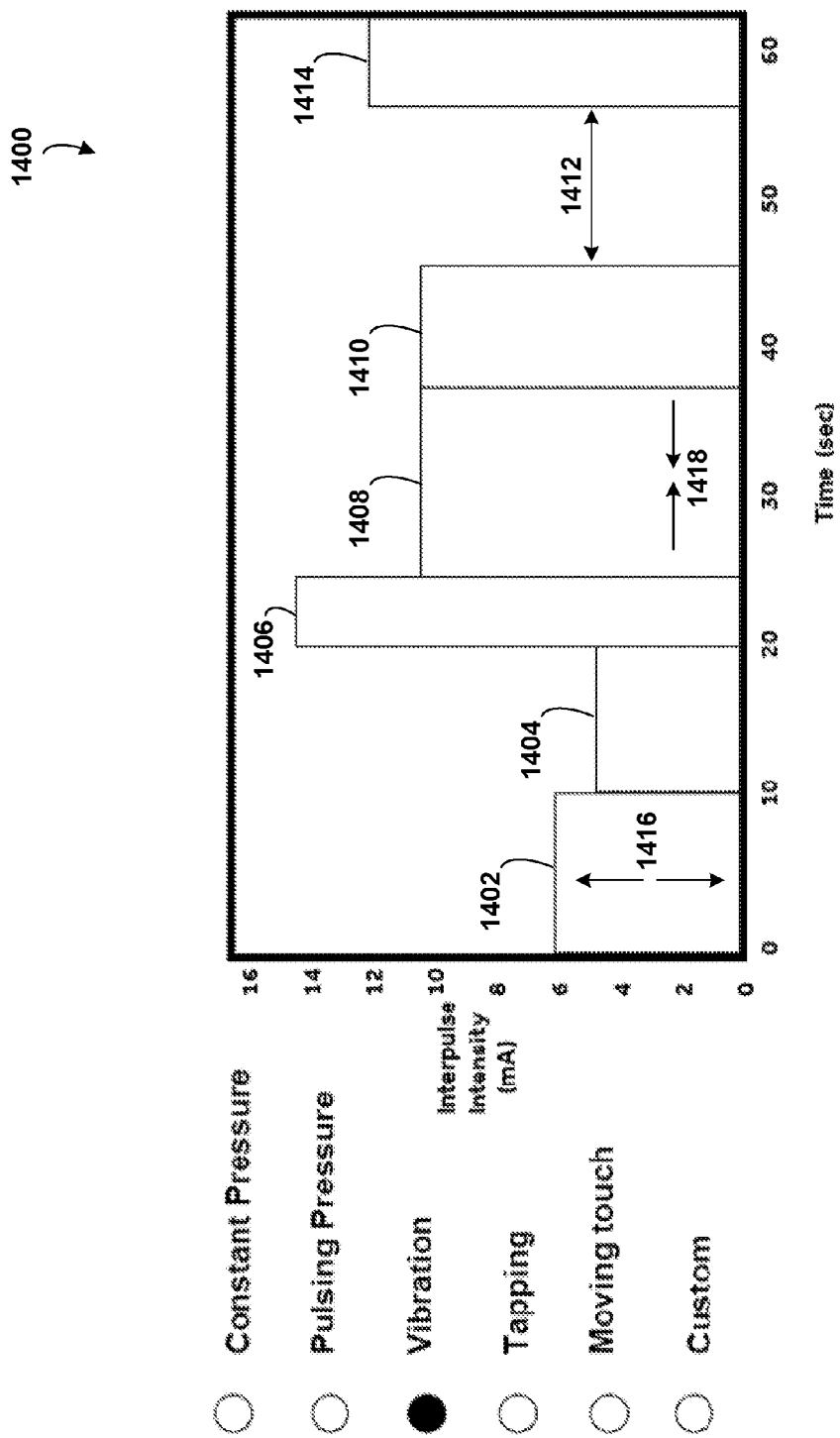
FIG. 14 is a conceptual diagram of a graphical user interface which may be displayed by a user interface of the programmer of FIG. 3.

For example, FIG. 14 illustrates an interface 1400 for mapping sensations to a particular interval over time. In this example, a user can drag various sensations into the interface 1400 and select relevant parameters, such as intensity, amplitude, pulse width, etc., using the interface 116 as shown in FIG. 6 for example, and time intervals to program the duration of the sensation. Dragging additional sensations into the interface 1400 allows more sensations to be delivered in a sequential, patterned fashion and on a time-programmable basis. For example, a constant pressure sensation may be mapped to interval 1402, a pulsing pressure sensation may be mapped to interval 1404, a vibration sensation may be mapped to interval 1406, a tapping sensation may be mapped to interval 1408, a moving touch sensation may be mapped to interval 1410, no sensation (e.g., no stimulation or stimulation that does not produce a sensation perceivable by the patient) may be mapped to interval 1412, and a custom sensation (see e.g., FIG. 13) may be mapped to interval 1414. Other examples are possible.

For example, it is contemplated that a user may interact directly with the interface 1400 to program desired properties or characteristics of a particular sensation. In the example of FIG. 13, a pinch gesture 1416 may be used to increase (or decrease) the intensity of the constant pressure sensation that is mapped to interval 1402. As another example, a pinch gesture 1418 may be used to decrease (or increase) the time duration of the interval 1408 associated with the tapping sensation as discussed above. Other examples are possible, whereby any setting or parameter mapped to the x- and y-axis may be similarly adjusted by direct interaction with the interface 1400. In addition, the overall time scale of the cycle shown in FIG. 13 may be adjusted by direct interaction the x-axis, such as via a "double-tap" or pinch gesture to extend the x-axis from 60 seconds to 120 seconds for example. Further, more or fewer intervals may be defined, and some sensations may be periodically or intermittently repeated during any given cycle. In general, the type and form of the programming may only be limited by the capabilities of the stimulation device used to generate stimulation to induce a desired sensation(s) over time.

Further, it is contemplated that such types of sequential sensations as discussed would loop or repeat unless cycling is used, which would discontinue therapy for a period of time. This may be preferred if sequentially moving between particular sensations has a strong therapeutic effect on a patient such that a therapy session is desired to last for a particular period of time, such as an hour, where pain relief may continue beyond the time that the stimulation is being delivered. Thus, another parameter to control in the context of the present disclosure is cycling. If a sensation such as pressure is felt, cycling the amplitude of the stimulation pulses on and off periodically would emulate a message where the pressure isn't constantly felt. For example, stimulation delivered for 2 seconds and off for 2 seconds would emulate a message. A gradual increase to the desired "on" intensity and a gradual decrease to the cycle "off" period could also be incorporated if the transition was too abrupt for the patient.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples of the disclosure have been described. These and other examples are within the scope of the following claims.

What is claimed is:

1. A patient programmer comprising:
a user interface configured to:
displaying, for each of a plurality of different stimulation sensations, a representation of the stimulation sensation, wherein each stimulation sensation of the plurality of stimulation sensations is associated with a respective set of therapy parameter values, the set of therapy parameter values representing a plurality of therapy parameters, wherein the representation of the stimulation sensation is different than the associated set of therapy parameter values, and wherein the plurality of different stimulation sensations includes at least one pressure sensation; and
receive user input that represents a selection of a stimulation sensation from among the plurality of different stimulation sensations; and
a processor configured to:
in response to the user input, select the respective set of therapy parameter values to control a medical device to deliver stimulation configured to induce the selected stimulation sensation,
wherein each respective set of therapy parameter values includes a first one or more therapy parameter values that define a respective, periodically-repeating modulation envelope, wherein the medical device modulates a second one or more of the therapy parameter values during a period comprising a plurality of stimulation pulses according to the modulation envelope, and wherein the second one or more therapy parameter values comprise at least one of pulse amplitude, pulse width, interpulse interval, or interburst interval.

2. The patient programmer of claim 1, wherein the user interface is configured to receive user input that represents an adjustment of at least one value of the selected set of therapy parameter values, and wherein the processor is configured to adjust the at least one value of the selected set of therapy parameter values to control the medical device to deliver stimulation in accordance with the adjustment of the at least one value.

3. The patient programmer of claim 1, further comprising:
telemetry circuitry configured to transmit the selected set of therapy parameter values to the medical device which is configured to deliver stimulation in accordance with the selected set of therapy parameter values to induce the selected stimulation sensation.

4. The patient programmer of claim 1,
wherein the user interface is configured to display an interactive control to receive the user input, and wherein the user input further represents an adjustment of the interactive control that is representative of an adjustment of intensity of the selected stimulation sensation, and
wherein the processor is configured to adjust at least one therapy parameter value of the selected set of therapy parameter values to control the medical device to deliver stimulation in accordance with the adjustment of intensity of the selected stimulation sensation.

5. The patient programmer of claim 1, wherein the stimulation sensation is selected from at least one of a constant pressure sensation, a pulsing pressure sensation, a vibration sensation, a tapping sensation or a moving touch sensation.

6. A method comprising:
by a patient programmer,
outputting for display, for each of a plurality of different stimulation sensations, a representation of the stimulation sensation, wherein each stimulation sensation of the plurality of stimulation sensations is associated with a respective set of therapy parameter values, the set of therapy parameter values representing a plurality of therapy parameters, wherein the representation of the stimulation sensation is different than the associated set of therapy parameter values, and wherein the plurality of different stimulation sensations includes at least one pressure sensation;
receiving user input that represents a selection of a stimulation sensation from among the plurality of different stimulation sensations;
selecting the respective set of therapy parameter values to control a medical device to deliver stimulation configured to induce the selected stimulation sensation,
wherein each respective set of therapy parameter values includes a first one or more therapy parameter values that define a respective, periodically-repeating modulation envelope, wherein the medical device modulates a second one or more of the therapy parameter values during a period comprising a plurality of stimulation pulses according to the modulation envelope, and wherein the second one or more therapy parameter values comprise at least one of pulse amplitude, pulse width, interpulse interval, or interburst interval.

7. The method of claim 6, further comprising:
receiving user input that represents adjustment of at least one value of the set of therapy parameter values;
adjusting the at least one value of the selected set of therapy parameter values; and
transmitting the selected value as adjusted to the medical device to control the medical device to deliver stimulation in accordance with the adjustment of the at least one value.

8. The method of claim 7, further comprising:
transmitting the selected set of therapy parameter values as adjusted to the medical device to control the medical device to deliver stimulation in accordance with the adjustment of the selected set of therapy parameter values.

9. The method of claim 6, further comprising:
outputting for display an interactive control to receive the user input, and wherein the user input further represents an adjustment of the interactive control that is representative of an adjustment of intensity of the selected stimulation sensation; and
adjusting the at least one therapy parameter value of the selected set of therapy parameter values to control the medical device to deliver stimulation in accordance with the adjustment of intensity of the selected stimulation sensation.

10. The method of claim 6, wherein the stimulation sensation is selected from at least one of a constant pressure sensation, a pulsing pressure sensation, a vibration sensation, a tapping sensation or a moving touch sensation.

11. A system comprising:
a patient programmer and a medical device, wherein the patient programmer is configured to:
output for display, for each of a plurality of different stimulation sensations, a representation of the stimulation sensation, wherein each stimulation sensation of the plurality of stimulation sensations is associated with a respective set of therapy parameter values, the set of therapy parameter values representing a plurality of therapy parameters, wherein the representation of the stimulation sensation is different than the associated set of therapy parameter values, and wherein the plurality of different stimulation sensations includes at least one pressure sensation;

receive user input that represents a selection of a stimulation sensation from among the plurality of different stimulation sensations;

select the respective set of therapy parameter values to control a medical device to deliver stimulation configured to induce the selected stimulation sensation; and transmit the values of the selected set of therapy parameter values to the medical device to control the medical device to induce the selected stimulation sensation, wherein each respective set of therapy parameter values includes a first one or more therapy parameter values that define a respective, periodically-repeating modulation envelope, wherein the medical device modulates a second one or more of the therapy parameter values during a period comprising a plurality of stimulation pulses according to the modulation envelope, and wherein the second one or more therapy parameter values comprise at least one of pulse amplitude, pulse width, interpulse interval, or interburst interval.

12. The system of claim 11, wherein the medical device is configured to:

receive from the patient programmer the values of the selected set of therapy parameter values; and generate stimulation in accordance with the values of the selected set of therapy parameter values to induce the selected stimulation sensation.

13. A non-transitory computer-readable storage medium comprising instructions, that when executed by processing circuitry of a patient programmer, cause the patient programmer to:

output for display, for each of a plurality of different stimulation sensations, a representation of the stimulation sensation, wherein each stimulation sensation of the plurality of stimulation sensations is associated with a respective set of therapy parameter values, the set of therapy parameter values representing a plurality of therapy parameters, and wherein the representation of the stimulation sensation is different than the associated set of therapy parameter values, and wherein the plurality of different stimulation sensations includes at least one pressure sensation;

detect user input that represents a selection of a stimulation sensation from among the plurality of different stimulation sensations; and based on the user input, select the respective set of therapy parameter values to control a medical device to deliver stimulation configured to induce the selected stimulation sensation, wherein each respective set of therapy parameter values includes a first one or more therapy parameter values that define a respective, periodically-repeating modulation envelope, wherein the medical device modulates a second one or more of the therapy parameter values during a period comprising a plurality of stimulation pulses according to the modulation envelope, and wherein the second one or more therapy parameter values comprise at least one of pulse amplitude, pulse width, interpulse interval, or interburst interval.

14. The patient programmer of claim 1, wherein the first one or more therapy parameter values comprise at least one of a frequency of repetition of the modulation envelope or a variance of the second one or more parameters within the modulation envelope.

* * * * *